US012697344B2

(12) United States Patent
Schatz et al.

(10) Patent No.: US 12,697,344 B2
(45) Date of Patent: Aug. 4, 2026

(54) THERAPEUTIC COMPOSITIONS, COMPONENTS AND METHODS OF PREPARATION AND USE THEREOF

(71) Applicant: Unique Flower LLC, Rainier, OR (US)

(72) Inventors: Daniel Schatz, Rainier, OR (US); Nicole Schatz, Rainier, OR (US)

( * ) Notice: Subject to any disclaimer, the term of this patent is extended or adjusted under 35 U.S.C. 154(b) by 0 days.

(21) Appl. No.: 18/124,519

(22) Filed: Mar. 21, 2023

(65) Prior Publication Data

US 2024/0316072 A1 Sep. 26, 2024

(51) Int. Cl.
| | |
|---|---|
| *A61K 31/00* | (2006.01) |
| *A61K 31/01* | (2006.01) |
| *A61K 36/185* | (2006.01) |
| *A61P 25/24* | (2006.01) |

(52) U.S. Cl.
CPC ............ *A61K 31/658* (2023.05); *A61K 31/01* (2013.01); *A61K 36/3482* (2024.05); *A61P 25/24* (2018.01)

(58) Field of Classification Search
CPC .... A61K 31/658; A61K 31/01; A61K 36/185; A61P 25/24
USPC ........................................................ 514/731
See application file for complete search history.

(56) References Cited

U.S. PATENT DOCUMENTS

| | | | |
|---|---|---|---|
| PP34,802 P2 * | 12/2022 | Schatz ........................... | Plt./258 |
| 12,029,722 B2 * | 7/2024 | Chistov ................ | A61K 31/353 |
| 2016/0250270 A1 * | 9/2016 | Wendschuh ....... | A61K 36/3482 |
| | | | 514/454 |
| 2020/0037638 A1 * | 2/2020 | Faraci .................. | A61K 9/1075 |

OTHER PUBLICATIONS

Sarris et al., Medicinal cannabis for psychiatric disorders: a clinically-focused systematic review, 2020, BMC Psychiatry, vol. 20 (24), p. 2 (Year: 2020).*

* cited by examiner

*Primary Examiner* — Jeffrey H Murray
*Assistant Examiner* — Rilla Marie Samsell
(74) *Attorney, Agent, or Firm* — Brian Youngjae Hyun

(57) ABSTRACT

Disclosed are compositions, components and dosage forms containing at least one cannabinoid as well as methods of preparation and use thereof. Compositions, components and/or dosage forms may include, based on the total weight of the composition, component or dosage form, about 10 wt % to about 25 wt % tetrahydrocannabinol (THC), about 0.001 wt % to about 1.0 wt % cannabidiol (CBD), about 0.01 wt % to about 5 wt % β-Myrcene, and about 0.01 wt % to about 5 wt % Ocimene 2.

17 Claims, 11 Drawing Sheets

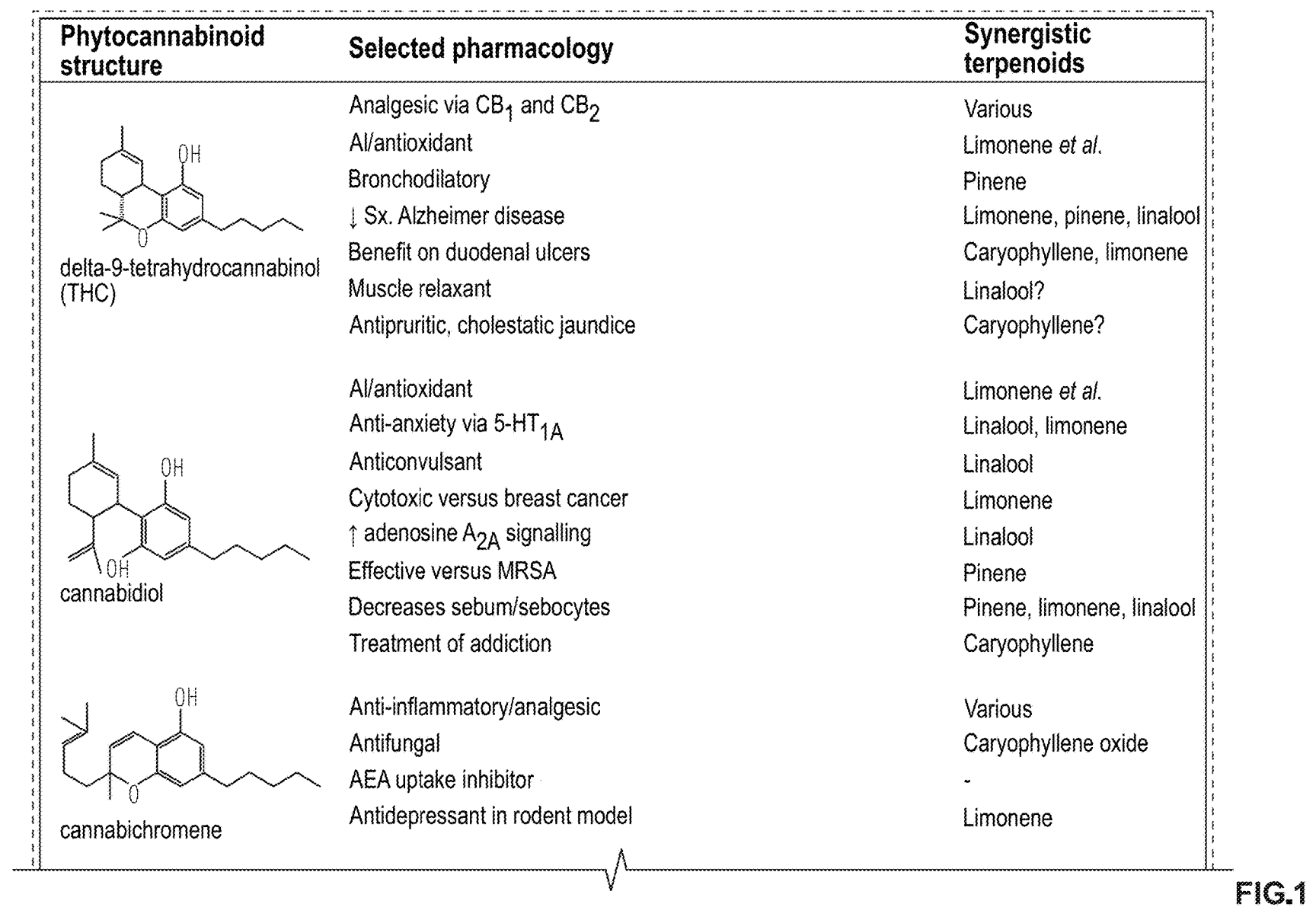

| Phytocannabinoid structure | Selected pharmacology | Synergistic terpenoids |
|---|---|---|
| delta-9-tetrahydrocannabinol (THC) | Analgesic via $CB_1$ and $CB_2$ | Various |
|  | AI/antioxidant | Limonene et al. |
|  | Bronchodilatory | Pinene |
|  | ↓ Sx. Alzheimer disease | Limonene, pinene, linalool |
|  | Benefit on duodenal ulcers | Caryophyllene, limonene |
|  | Muscle relaxant | Linalool? |
|  | Antipruritic, cholestatic jaundice | Caryophyllene? |
| cannabidiol | AI/antioxidant | Limonene et al. |
|  | Anti-anxiety via $5\text{-}HT_{1A}$ | Linalool, limonene |
|  | Anticonvulsant | Linalool |
|  | Cytotoxic versus breast cancer | Limonene |
|  | ↑ adenosine $A_{2A}$ signalling | Linalool |
|  | Effective versus MRSA | Pinene |
|  | Decreases sebum/sebocytes | Pinene, limonene, linalool |
|  | Treatment of addiction | Caryophyllene |
| cannabichromene | Anti-inflammatory/analgesic | Various |
|  | Antifungal | Caryophyllene oxide |
|  | AEA uptake inhibitor | , |
|  | Antidepressant in rodent model | Limonene |

FIG.1

| | | |
|---|---|---|
| cannabigerol | TRPM8 antagonist prostate cancer | Cannabis terpenoids |
| | GABA uptake inhibitor | Phytol, linalool |
| | Anti-fungal | Caryophyllene oxide |
| | Antidepressant rodent model | Limonene |
| | 5-HT$_{1A}$ antagonism | |
| | Analgesic, α-2 adrenergic blockade | Various |
| | ↓ Keratinocytes in psoriasis | adjunctive role? |
| | Effective versus MRSA | Pinene |
| | AI/anti-hyperalgesic | Caryophyllene et al.... |
| | Treatment of metabolic syndrome | – |
| tetrahydrocannabivarin | Anticonvulsant | Linalool |
| | Inhibits diacylglycerol lipase | – |
| cannabidivarin | Anticonvulsant in hippocampus | Linalool |
| | Sedative | Nerolidol, myrcene |
| | Effective versus MRSA | Pinene |
| | TRPV2 agonist for burns | Linalool |
| | ↓ keratinocytes in psoriasis | adjunctive role? |
| cannabinol (CBN) | ↓ breast cancer resistance protein | Limonene |

5-HT, 5-hydroxytryptamine (serotonin); AEA, arachidonoylethanolamide (anandamide); AI,anti-inflammatory; CB1/CB2, Cannabinoid receptor 1 or 2; GABA, gamma aminobutyric acid; TRPV, transient receptor potential vanilloid receptor; MRSA, methicillin-resistant Staphylococcus aureus; Sx, symptoms.

FIG. 1 (Cont.)

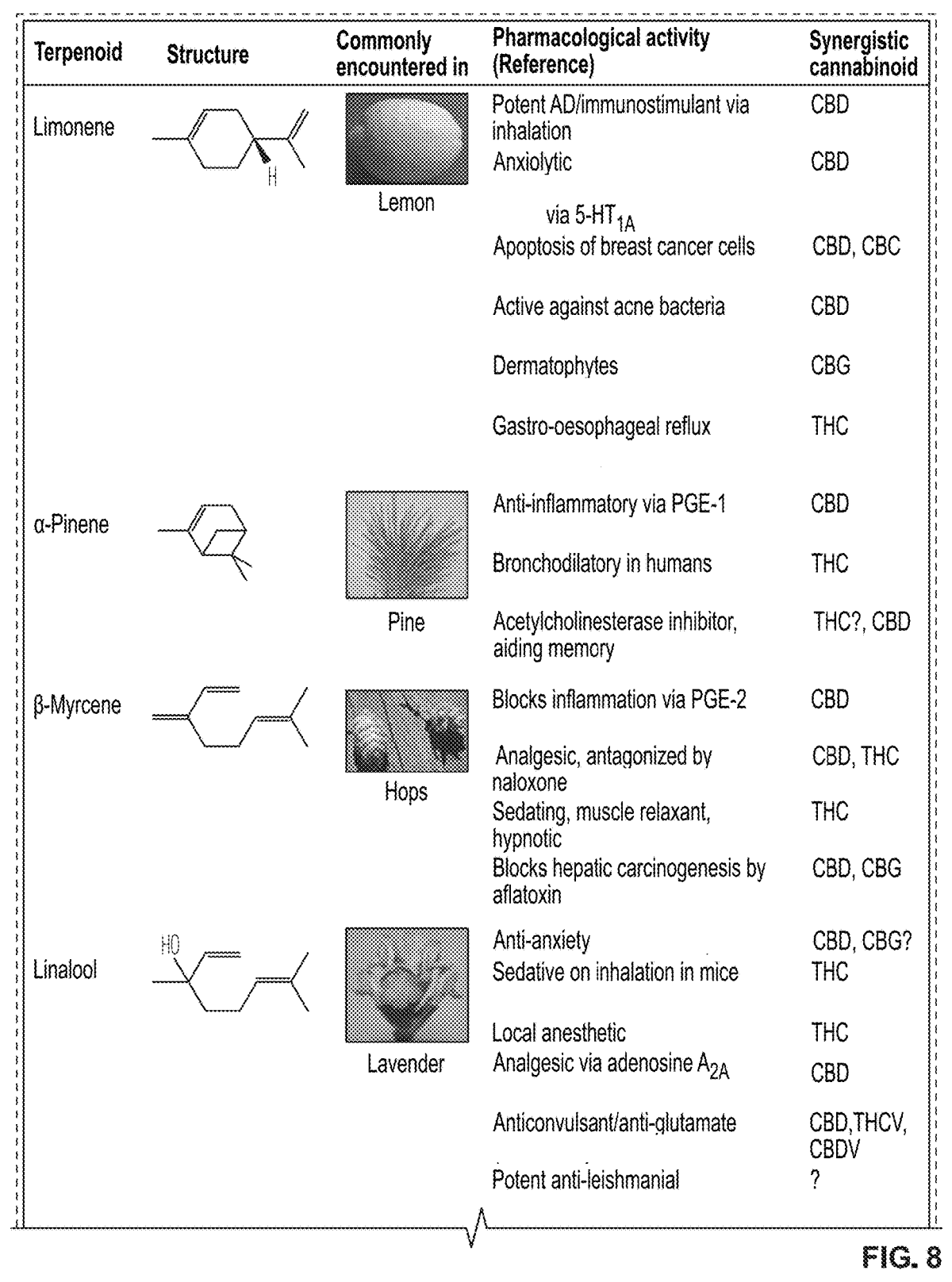

| Terpenoid | Structure | Commonly encountered in | Pharmacological activity (Reference) | Synergistic cannabinoid |
|---|---|---|---|---|
| Limonene | | Lemon | Potent AD/immunostimulant via inhalation | CBD |
| | | | Anxiolytic | CBD |
| | | | via 5-HT$_{1A}$ | |
| | | | Apoptosis of breast cancer cells | CBD, CBC |
| | | | Active against acne bacteria | CBD |
| | | | Dermatophytes | CBG |
| | | | Gastro-oesophageal reflux | THC |
| α-Pinene | | Pine | Anti-inflammatory via PGE-1 | CBD |
| | | | Bronchodilatory in humans | THC |
| | | | Acetylcholinesterase inhibitor, aiding memory | THC?, CBD |
| β-Myrcene | | Hops | Blocks inflammation via PGE-2 | CBD |
| | | | Analgesic, antagonized by naloxone | CBD, THC |
| | | | Sedating, muscle relaxant, hypnotic | THC |
| | | | Blocks hepatic carcinogenesis by aflatoxin | CBD, CBG |
| Linalool | | Lavender | Anti-anxiety | CBD, CBG? |
| | | | Sedative on inhalation in mice | THC |
| | | | Local anesthetic | THC |
| | | | Analgesic via adenosine A$_{2A}$ | CBD |
| | | | Anticonvulsant/anti-glutamate | CBD, THCV, CBDV |
| | | | Potent anti-leishmanial | ? |

FIG. 8

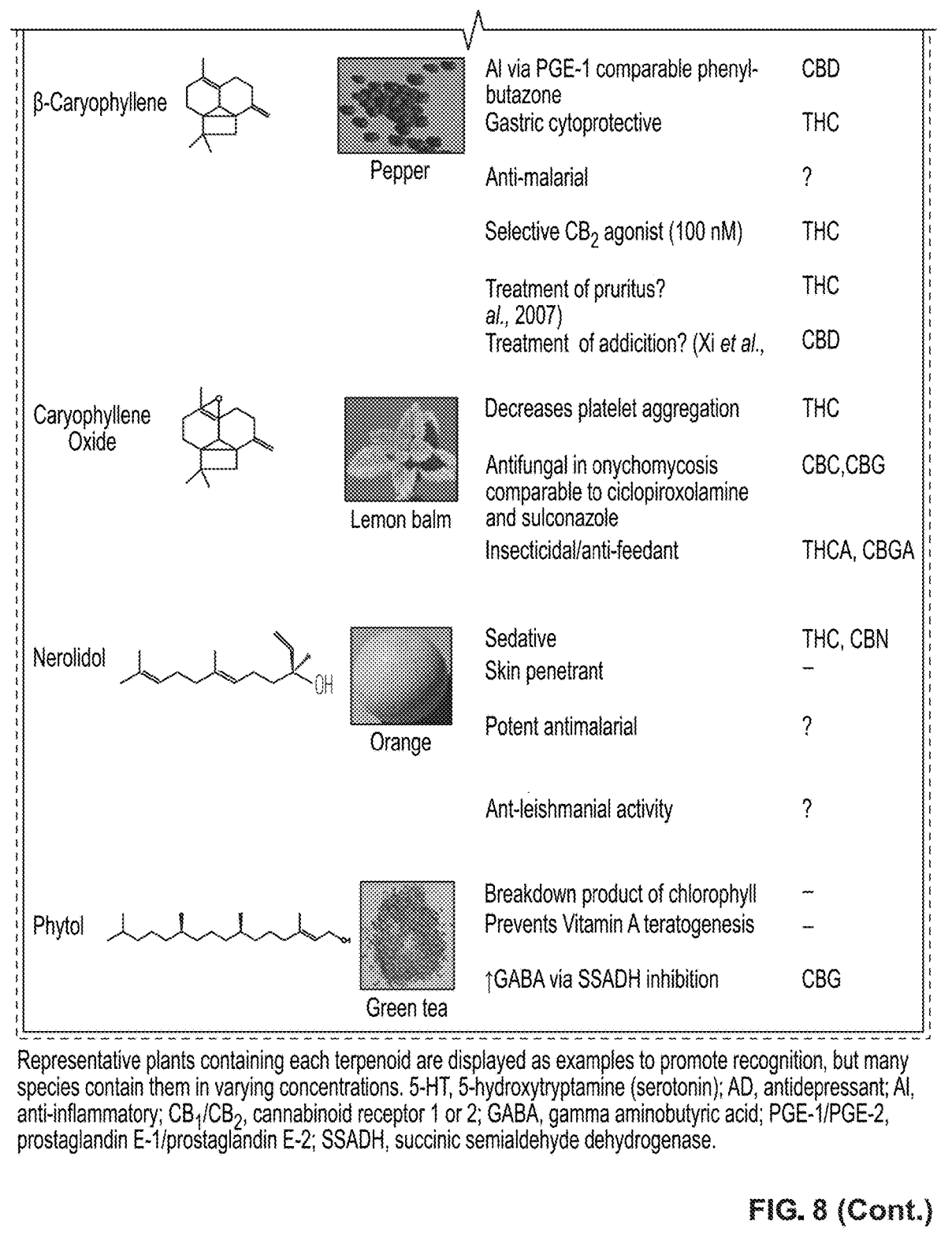

| β-Caryophyllene | Pepper | AI via PGE-1 comparable phenyl-butazone | CBD |
| | | Gastric cytoprotective | THC |
| | | Anti-malarial | ? |
| | | Selective CB$_2$ agonist (100 nM) | THC |
| | | Treatment of pruritus? al., 2007) | THC |
| | | Treatment of addicition? (Xi et al., | CBD |
| Caryophyllene Oxide | Lemon balm | Decreases platelet aggregation | THC |
| | | Antifungal in onychomycosis comparable to ciclopiroxolamine and sulconazole | CBC,CBG |
| | | Insecticidal/anti-feedant | THCA, CBGA |
| Nerolidol | Orange | Sedative | THC, CBN |
| | | Skin penetrant | – |
| | | Potent antimalarial | ? |
| | | Ant-leishmanial activity | ? |
| Phytol | Green tea | Breakdown product of chlorophyll | – |
| | | Prevents Vitamin A teratogenesis | – |
| | | ↑GABA via SSADH inhibition | CBG |

Representative plants containing each terpenoid are displayed as examples to promote recognition, but many species contain them in varying concentrations. 5-HT, 5-hydroxytryptamine (serotonin); AD, antidepressant; AI, anti-inflammatory; CB$_1$/CB$_2$, cannabinoid receptor 1 or 2; GABA, gamma aminobutyric acid; PGE-1/PGE-2, prostaglandin E-1/prostaglandin E-2; SSADH, succinic semialdehyde dehydrogenase.

FIG. 8 (Cont.)

THERAPEUTIC COMPOSITIONS, COMPONENTS AND METHODS OF PREPARATION AND USE THEREOF

FIELD

The present invention relates to therapeutic compositions, components, dosage forms and methods of preparation and use thereof.

BACKGROUND

*Cannabis* plants contain over 400 compounds including cannabinoids, terpenes, esters, thiols and alcohols, and more than 2,000 compounds are produced through pyrolysis while smoking. *Cannabis* research is ongoing in relation to a variety of potential medicinal effects. There have been numerous reports documenting the therapeutic utility of various cannabinoids most notably cannabidiol (CBD) and tetrahydrocannabinol (THC), in particular, $\Delta^9$-tetrahydro-cannabinol. Although both trans-(−)-$\Delta^9$-THC and its optical isomer trans-(+)-$\Delta^9$-THC are reported to be useful, for example, to treat pain, the trans-(−)-$\Delta^9$-THC enantiomer has been identified as the more potent of the two enantiomers.

*Cannabis* has been reported to benefit patients suffering from a wide range of symptoms experienced in connection with serious medical conditions. For example, cannabis has been used to alleviate symptoms associated with cancer, anorexia, AIDS, chronic pain, muscle spasticity, glaucoma, arthritis, migraine and many other illnesses. *Cannabis* is recognized as having anti-emetic properties and has been successfully used to treat nausea and vomiting in cancer patients undergoing chemotherapy. Studies also report use of cannabis in treating the weight loss syndrome of AIDS and for the treatment of glaucoma by reducing intraocular pressure. Furthermore, cannabis is known for its muscle relaxing and anti-convulsant effects.

The most prevalent mode of administration of cannabis is by smoking. However, many patients find the act of smoking unappealing, as well as generally unhealthy. There is a need for improved compositions having numerous medicinal benefits and for new methods of administering cannabis to subjects in need thereof.

BRIEF SUMMARY

Disclosed herein are embodiments of compositions, comprising: a cannabis component, comprising tetrahydrocannabinol (THC), cannabidiol (CBD), and at least one of β-Myrcene or Ocimene 2, and one or more additive.

Further disclosed are embodiments of cannabis components, comprising, tetrahydrocannabinol (THC), cannabidiol (CBD), and at least one of β-Myrcene or Ocimene 2.

In further embodiments, disclosed are dosage forms comprising: a cannabis component, comprising: tetrahydrocannabinol (THC), cannabidiol (CBD), at least one of β-Myrcene or Ocimene 2; and a pharmaceutically acceptable excipient.

Additionally disclosed herein are *Cannabis sativa* plants, comprising: tetrahydrocannabinol (THC); cannabidiol (CBD); β-Myrcene; and Ocimene 2.

A method of growing a cannabis plant, wherein the cannabis plant comprises: tetrahydrocannabinol (THC); cannabidiol (CBD); β-Myrcene; and Ocimene 2, the method comprising: planting the cannabis plant; growing the cannabis plant for about 14 weeks to about 16 weeks; and harvesting the cannabis plant.

Further disclosed herein are methods of preparing a composition, comprising: extracting a cannabis component from a cannabis plant, wherein the cannabis component comprises: tetrahydrocannabinol (THC); cannabidiol (CBD); β-Myrcene; and Ocimene.

In further embodiments, disclosed are methods of preparing a dosage form, comprising: combining a cannabis component with a pharmaceutically acceptable excipient, wherein the cannabis component comprises, based on the total weight of the composition: tetrahydrocannabinol (THC); cannabidiol (CBD); at least one of β-Myrcene or Ocimene; and a pharmaceutically acceptable excipient; and forming the dosage form.

In one or more embodiments, disclosed herein are methods of treating anxiety in a subject in need thereof, comprising: administering to the subject, at least one of: a composition according to embodiments, a cannabis component according to embodiments, or a dosage form according to embodiments.

Additionally disclosed are methods of treating depression in a subject in need thereof, comprising: administering to the subject, at least one of: a composition according to embodiments, a cannabis component according to embodiments, or a dosage form according to embodiments.

In various embodiments, disclosed herein are methods of stimulating at least one of positivity of thought or mental function in a subject, comprising: administering to the subject, at least one of: a composition according to embodiments, a cannabis component according to embodiments, or a dosage form according to embodiments.

According to further embodiments, disclosed herein are methods of treating inflammation in a subject, comprising: administering to the subject, at least one of: a composition according to embodiments, a cannabis component according to embodiments, or a dosage form according to embodiments.

In yet further embodiments, disclosed herein are methods of treating a neurological disorder in a subject, comprising: administering to the subject, at least one of: a composition according to embodiments, a cannabis component according to embodiments, or a dosage form according to embodiments.

BRIEF DESCRIPTION OF THE DRAWINGS

The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIG. 1 shows the structures of several phytocannabinoids that may be present in a cannabis plant.

FIG. 8 shows the structures of several terpenoids present in a cannabis plant.

DETAILED DESCRIPTION

Figure 2:
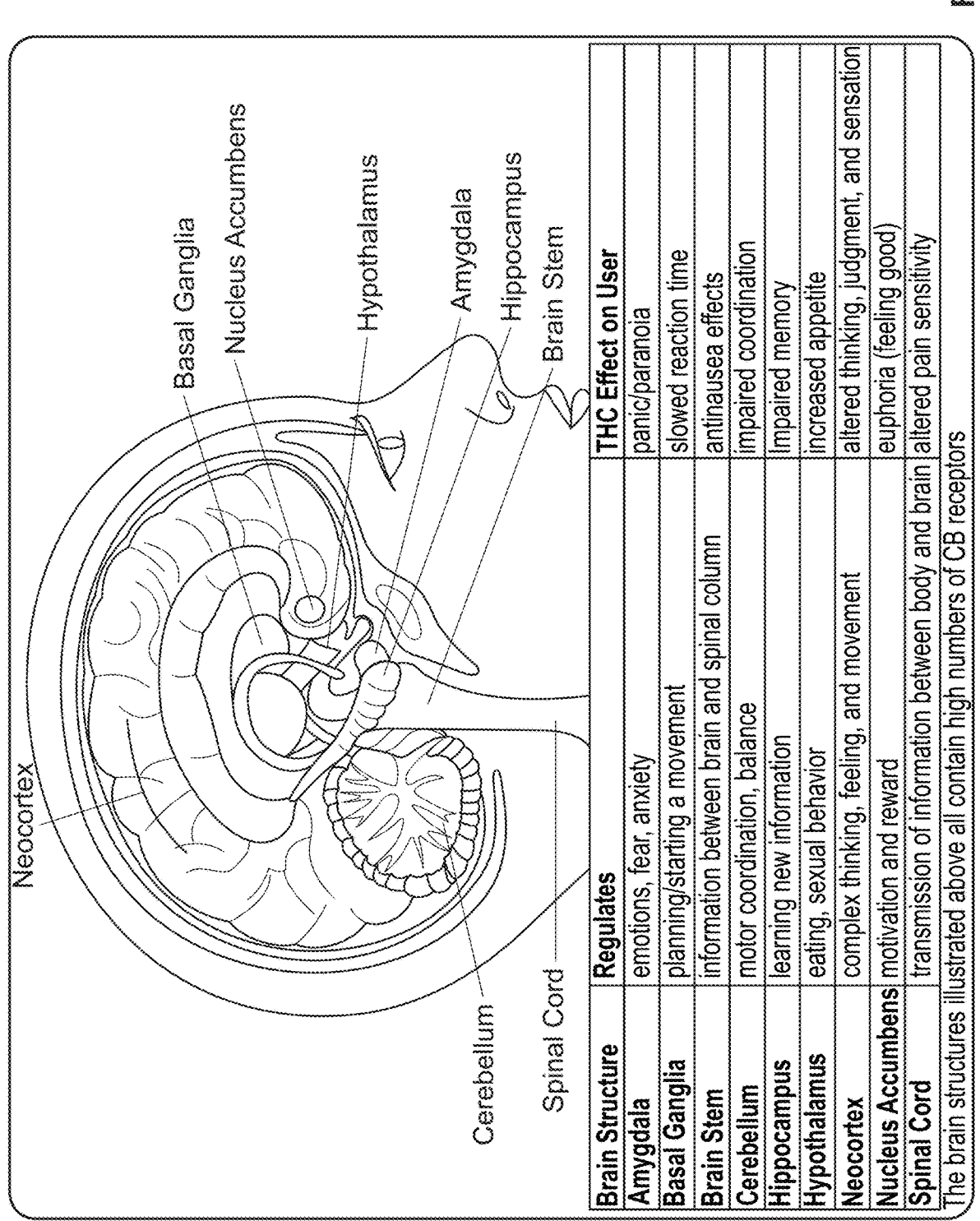
FIG. 2 depicts the structures of the brain and indicates the effects of THC on cannabinoid receptors within the various brain structures.

Described herein are embodiments of cannabis compositions, components, dosage forms and methods of preparation and use thereof that include at least one cannabinoid. In one or more embodiments, the compositions include ingredients and/or components that are derived from cannabis plants having the UNIQUE FLOWER ORIGINAL HAZE chemotype, wherein seeds of such plant may be deposited in an acceptable depository in accordance with the Budapest Treaty. This chemotype is a characterized by inter alia a combination of cannabinoids and terpenes that can be extracted from the plant. Also disclosed are methods of making and using such compositions and dosage forms for treating a variety of diseases and/or disorders.

The endocannabinoid system (ECS) is a vast network of chemical signals and cellular receptors, which are densely packed throughout the human body including the brain. The ECS involves numerous organs and cell types. Two known cannabinoid receptors, cannabinoid receptor type 1 (CB1) and cannabinoid receptor type 2 (CB2), are involved in the function of the ECS. CB1 receptors are most densely located in the CNS while CB2 receptors are abundant in the immune system, peripheral nervous system, arteries, heart, spleen, the urinary systems, reproductive systems, the gastrointestinal tracts and the endocrine glands. The ECS also includes two endogenous lipids (also referred to as endocannabinoids) that are produced by the body and engage the CB1 and CB2 receptors: anandamide (AEA) and 2-Arachidonoylglycerol (2-AG). AEA, known as the "bliss molecule," helps to modulate brain reward circuitry. The other endocannabinoid, 2-AG, is involved in several (patho)physiological functions such as emotion, cognition, energy balance, pain sensation and neuroinflammation.

CB1 receptors in the brain outnumber many of the other receptor types in the brain. CB1 receptors control the levels and activity of most other neurotransmitters. These receptors regulate by immediate feedback, turning up or down the activity of a system needs that needs to be adjusted (e.g., systems related to hunger, temperature or alertness). To stimulate CB1 receptors, human bodies produce molecules called endocannabinoids having a structural similarity to molecules in cannabis plants.

CB2 receptors exist mostly in immune tissues and are critical for controlling immune function. CB2 receptors play a role in modulating intestinal inflammation, contraction and pain in inflammatory bowel conditions. CB2 receptors are particularly interesting targets of drug development because they do not cause a high associated with cannabis that stimulating the CB1 receptors does (which is often an unwanted side effect).

The human body produces two endocannabinoids: anandamide (AEA) and 2-arachidonoylglycerol (2-AG). These endocannabinoids are produced as needed to regulate systems in the body. Cannabis plants produce several phytocannabinoids. FIG. 1 shows the structures of several phytocannabinoids. When introduced into the human body, phytocannabinoids together with endocannabinoids interact with the CB1 and CB2 receptors in the ECS to produce a variety of effects.

FIG. 2 depicts the structures of the brain involved in the endocannabinoid system (ECS). These structures include the amygdala, basal ganglia, brain stem, cerebellum, hippocampus, hypothalamus, neocortex, nucleus accumbens and spinal cord. As shown in FIG. 2, the amygdala regulates emotions, fear and anxiety. The basal ganglia regulate planning and/or starting a movement. The brain stem regulates information between the brain and spinal column. The cerebellum regulates motor coordination and balance. The hippocampus regulates the learning of new information. The hypothalamus regulates eating and sexual behavior. The neocortex regulates complex thinking, feeling and movement. The nucleus accumbens regulates motivation and reward. Finally, the spinal cord regulates transmission of information between the body and the brain.

As mentioned above, the interaction of cannabinoids with CB1 and CB2 receptors in the body produces a variety of effects. For example, as shown in FIG. 2, when THC binds with receptors in the amygdala, the resulting effects can include panic and/or paranoia. The interaction of THC with receptors in the basal ganglia can slow reaction time. When THC interacts with receptors in the brain stem, antinausea effects are produced. The effects of THC in the cerebellum include impaired coordination and, in the hippocampus, impaired memory. The interaction of THC with receptors in the hypothalamus causes increased appetite and, in the neocortex, altered thinking judgement and sensation. When THC interacts with receptors in the nucleus accumbens, euphoria effects are produced and in the spinal cord, altered pain sensitivity is produced.

β-Caryophyllene (BCP) is an agonist of CB2 receptors and promotes anti-inflammatory action by inhibiting inflammatory mediators. BCP through its anti-inflammatory properties improved treatment of nervous system diseases, atherosclerosis, and tumors. In many neurodegenerative diseases, amyotrophic lateral sclerosis, and in some tumors, the expression of CB2 receptors is increased. This allows for cannabinoids and terpenes found in The Unique Flower Original Haze, specifically BCP, to function and initiate an anti-inflammatory response. While not directly interacting with the CB1 receptors, BCP binding to CB2 receptors initiates an increase in the intracellular levels of $Ca^{2+}$ which are directly responsible for the production of AEA and 2-AG. CB2 receptors function in numerous pathological processes and is an interesting molecule to look at for the treatment of many types of pathological conditions. In pre-clinical studies BCP has been shown to be a modulator of the nervous system and helps to treat many neurodegenerative and inflammatory issues. Nitric Oxide (NO), an inflammation mediator, is one of the characteristics of neuroinflammation. BCP acts on inducible nitric oxide synthase (iNOS) which in turn reduces the amount of NO in the brain. NO is also involved in activating an enzyme which is a precursor to prostaglandins which are responsible for inflammation and pain. BCP can also act independent of binding to the CB2 receptors and induce neurogenesis in the brain. BCP has been shown to be a possible substitute for anxiolytics and antidepressants.

Figure 3:
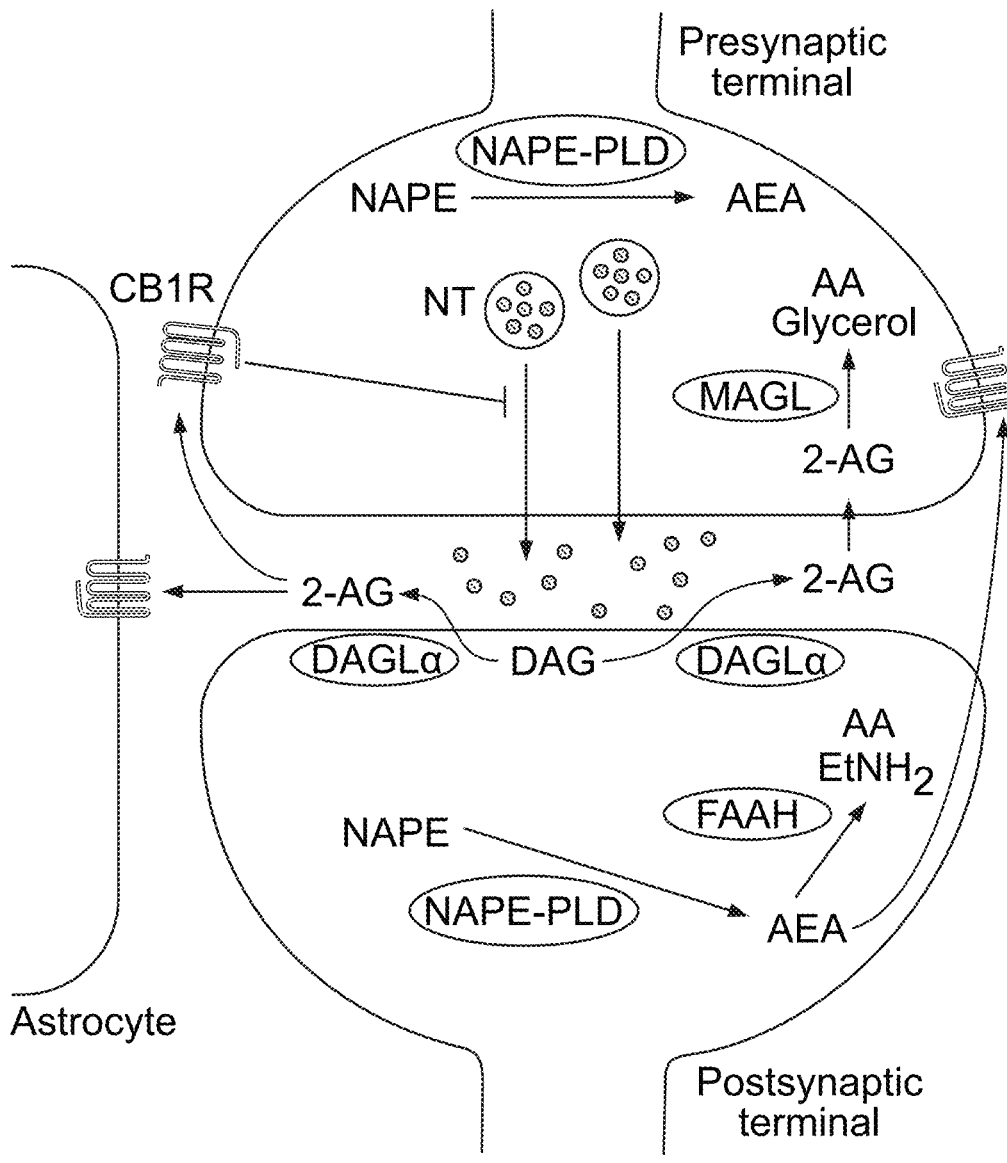
FIG. 3 depicts the pathways of endocannabinoids within the brain, for example, the effects of anandamide (AEA) on the frontal cortex and dorsal striatum, parts of the brain involved in the control of anxiety and stress responses.

FIG. 3 depicts the pathways of endocannabinoids within the brain, for example, the effects of AEA on the frontal cortex and dorsal striatum, parts of the brain involved in the control of anxiety and stress responses. Anxiety and stress affect a constellation of physiological systems in the body and evokes a rapid shift in many neurobehavioral processes. A growing body of work indicates that the endocannabinoid (eCB) system is an integral regulator of the stress response. Across a wide array of stress paradigms, stress evokes bidirectional changes in AEA and 2-AG, with stress exposure reducing AEA levels and increasing 2-AG levels. In almost every brain region examined, exposure to chronic stress reliably causes a downregulation or loss of cannabinoid type 1 (CB1) receptors.

The simplified scheme shown in FIG. 3 shows endocannabinoid retrograde signaling mediated synaptic transmission. Endocannabinoids are produced from postsynaptic terminals upon neuronal activation. 2-AG is biosynthesized from diacylglycerol (DAG) by diacylglycerol lipase-α (DAGLα), and AEA is synthesized from N-acyl-phosphatidylethanolamine (NAPE) by NAPE-specific phospholipase D (NAPE-PLD). As lipids, endocannabinoids (mostly 2-AG) readily cross the membrane and travel in a retrograde fashion to activate CB1 receptors (CB1Rs) located in the presynaptic terminals. Activated CB1Rs inhibit neurotransmitter (NT) release through the suppression of calcium influx. 2-AG is also able to activate CB1Rs located in astrocytes, leading to the release of glutamate. Extra 2-AG in the synaptic cleft is taken up into the presynaptic terminals, via a yet unclear mechanism, and degraded to arachidonic acid (AA) and glycerol by monoacylglycerol lipase (MAGL). On the other hand, AEA, synthesized in postsynaptic terminal, activates intracellular CB1R and other non-CBR targets, such as the transient receptor potential cation channel subfamily V member 1 (TRPV1). Although endocannabinoid retrograde signaling is mainly mediated by 2-AG, AEA can activate presynaptic CB1Rs as well. Fatty acid amide hydrolase (FAAH) is primarily found in postsynaptic terminals and is responsible for degrading AEA to AA and ethanolamine (EtNH2).

Figure 4:
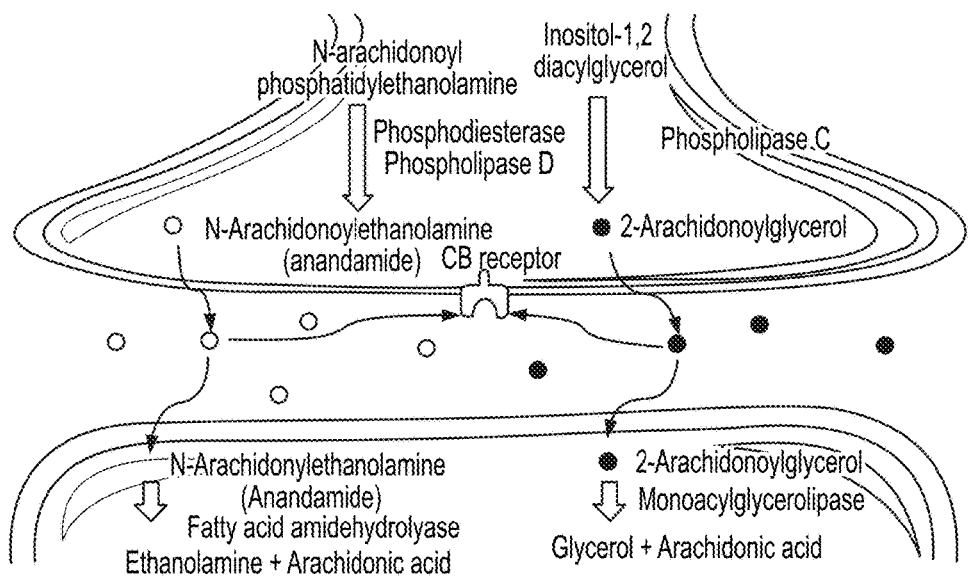
FIG. 4 is a diagram showing the formation of endocannabinoids 2-Arachidonoylglycerol (2-AG) and AEA within the body.

FIG. 4 is a diagram showing the formation of endocannabinoids 2-AG and AEA within the body. As shown in FIG. 4, AEA is synthesized from the precursor N-arachidonoyl phosphatidylethanolamine by phosphodiesterase phospholipase D enzyme. Once anandamide is synthesized, it is released from the neuronal terminal in a calcium ion-dependent manner and binds to presynaptic cannabinoid receptors. AEA is then rapidly taken up by neurons and astrocytes where it is degraded by FAAH into ethanolamine and arachidonic acid. The other endogenous cannabinoid, 2-AG is synthesized by the hydrolysis of an inositol-1,2-diacylglycerol by phospholipase C. Similar to AEA, 2-AG binds to cannabinoid receptors and undergoes rapid biological degradation and catalytic hydrolysis, which is mediated by monoacylglycerol lipase (MGL).

Figure 5:
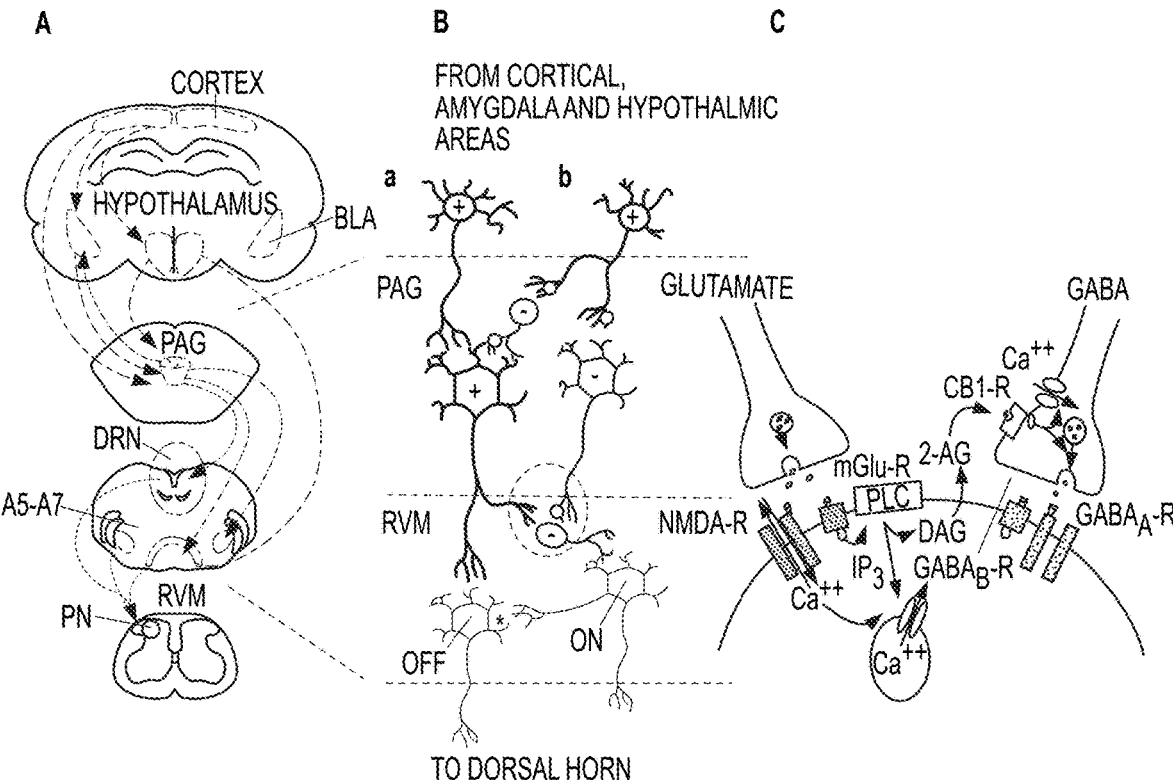
FIG. 5 shows a diagrammatical representation of an endocannabinoid synapse.

FIG. 5 shows a diagrammatical representation of an endocannabinoid synapse; a possible mechanism for endocannabinoid-mediated control of nociception. Nociception is when sensory neurons transmit painful stimulus at the spinal and supraspinal level. FIG. 5(A) shows some of the interactions between various brain regions of the descending pain pathway. The periaqueductal gray (PAG) receives critical input from various cortical areas as well as from the hypothalamus and amygdala. The net input of afferent neurons to the PAG determines the firing of the various PAG cell types.

As shown in FIG. 5(B), there are two possible outcomes of this net input. In resting conditions (no pain) the sum effect on the input of ON and OFF cells to the dorsal horn is neutral. Painful stimuli are proposed to selectively activate pathway (b), where these excitatory neurons from pathways upstream of the PAG project onto inhibitory projection neurons (possibly GABAergic) as well as inhibitory GABAergic interneurons. This activation of inhibitory interneurons in the PAG prevents firing of excitatory projection neurons (possibly glutamate) and negatively impacts on OFF cells in the RVM. Simultaneously, GABAergic projection neurons from the PAG synapse on GABAergic interneurons in the RVM and disinhibit their suppression of firing of ON neurons to result in nociception. The mediation of antinociception is achieved through pathway (a), when excitatory neurons from pathways upstream of the PAG activate excitatory neurons in the PAG. These excitatory neurons in turn activate the firing of OFF cells and inhibit the firing of ON cells through GABAergic interneurons. It is also proposed that the activity of OFF cells negatively impacts on the firing of ON cells through an inhibitory mechanism and possibly impacts on OFF-cell duration (represented by an asterisk).

FIG. 5(C) further shows the circled section of (B), illustrates the possible mechanism behind cannabinoid-mediated antinociception. The activation of various receptor subtypes leads to an increase in intracellular calcium by various pathways. This increase in calcium concentration initiates endocannabinoid synthesis and release. The released endocannabinoids can then prevent the presynaptic release of neurotransmitters possibly by inhibiting calcium influx or vesicular release of neurotransmitters.

As shown in FIG. 5, ligand gated chlorine channels help mediate major inhibitory functions in the CNS by allowing GABA inhibitors to pass through the chlorine channel. Terpenes interact with GABA type A Receptors to initiate a Chlorine (Cl⁻) channel, which leads to neuronal inhibition and has an AX effect. In the human hippocampal region of the brain, extracellular release of GABA was modulated by endocannabinoids and cannabinoid receptor agonists. The ECS system is also involved in GABA mediated nociception (FIG. 5). Terpenes release 5-HT2A receptor antagonists, which have been shown to have antipsychotic and antidepressant properties in pre-clinical trials (FIG. 5). Altering serotonin reuptake and release levels can help overcome stress. Terpenes also interact with Adenosine A2A receptors as agonists, which are involved in increased $Ca^{2+}$ flow over NMDA channels (FIG. 5). Beta-Pinene, found in The Unique Flower Original Haze, is one terpene that has been shown to interact with Dopamine receptors in the brain, specifically D1 receptors (FIG. 5). Inhalation of terpenes, specifically monoterpenes, has been shown to enhance terpene activity because of direct access to the CNS. Sesquiterpenes have also been shown to have AD effects. BCP acting as a CB2 receptor agonist was shown to reduce depressive symptoms in mice by activating the CB2 receptors. An example of a plant-based terpene, hyperforin, extract from *H. perforatum*, is a known antidepressant. Like other antidepressants available on the market, hyperforin acts by inhibiting serotonin, dopamine and norepinephrine as well as inhibiting GABA neurotransmitters.

Figures 6, 7:
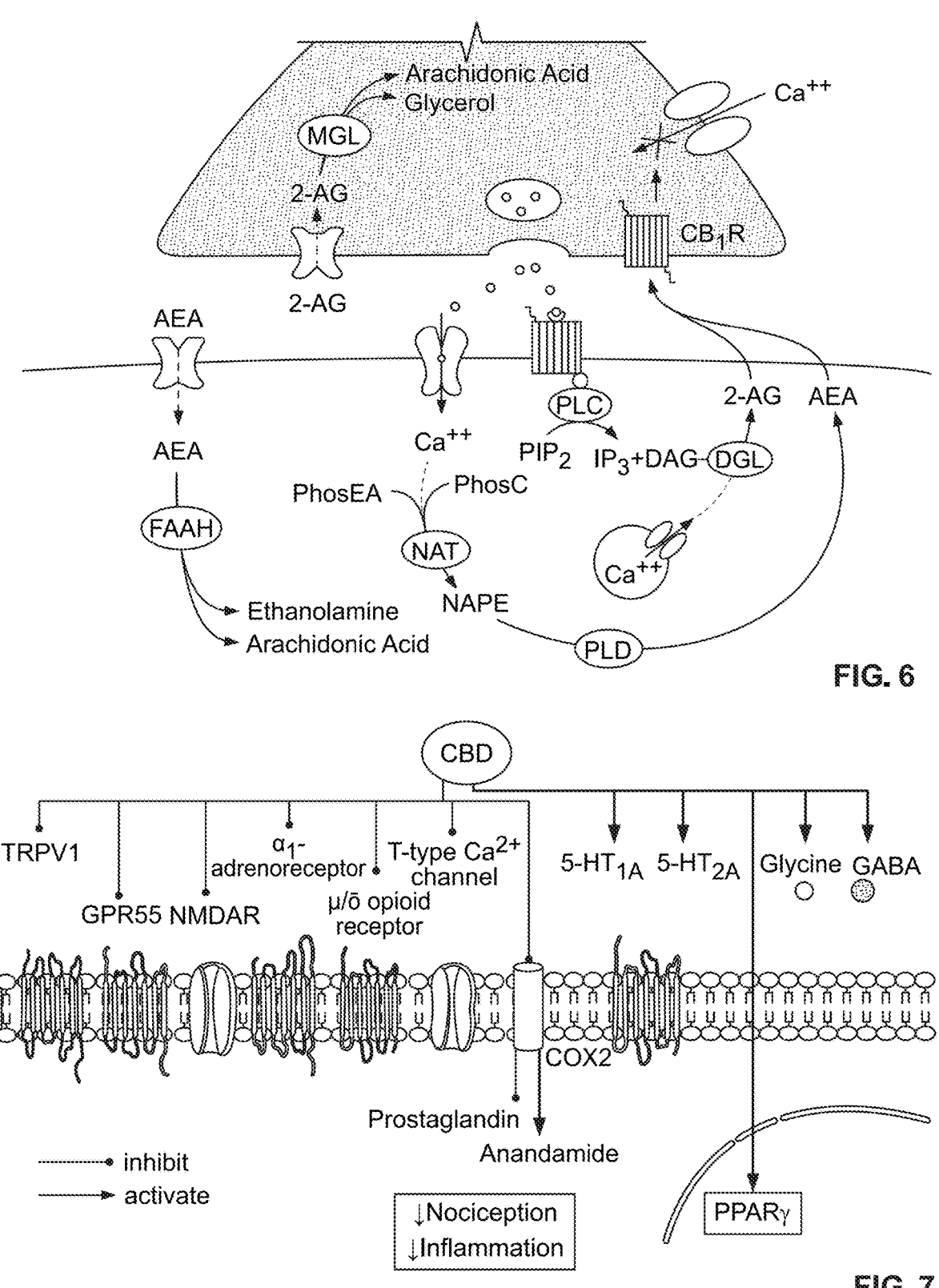
FIG. 6 shows a mechanism for endocannabinoid-mediated control of nociception.
FIG. 7 shows a diagram indicating the anti-nociceptive properties of CBD.

FIG. 6 shows a mechanism for endocannabinoid-mediated control of nociception and provides a diagrammatical representation of an endocannabinoid synapse. AEA and 2-AG are synthesized following an increase in cytosolic calcium ($Ca^{++}$) resulting from activation of postsynaptic ion channels or G protein-coupled receptors. The activation of Gq protein-coupled receptors results in the synthesis of inositol trisphosphate (IP3) and diacylglycerol (DAG) from phosphatidylinositol bisphosphate (PIP2). IP3 mobilizes calcium release from intracellular stores triggering the formation of 2-AG from DAG by the enzyme diacylglycerol lipase (DGL). The activation of Ca++ gating ion channels facilitates the influx of Ca++, which leads to the formation of N-arachidonoyl-phosphatidylethanolamine (NAPE) from phosphatidylethanolamine (PhosEA) and phosphatidylcholine (PhosC) via the enzyme N-acyltransferase (NAT). NAPE is then hydrolyzed to anandamide by a phospholipase D-type enzyme (NAPE-PLD). The cannabinoids are released from the postsynaptic neuron and travel retrogradely to the presynaptic membrane to activate cannabinoid receptors (e.g., cannabinoid1 receptor, CB1R). The activation of the CB1 receptor results in inhibition of Ca++ channels in the presynaptic membrane and a number of other signal transduction-mediated events, which generally result in suppression of neuronal activity and neurotransmitter release. 2-AG is catabolized to arachidonic acid and glycerol by monoacylglycerol lipase (MGL), while FAAH breaks down AEA to arachidonic acid and ethanolamine.

FIG. 7 shows a diagram representing the anti-nociceptive properties of CBD. Without being bound by any particular theory, it is believed that the analgesic effects of CBD may be due to the suppression of TRPV1, GPR55, NMDAR and α1-adrenoreceptors, T-type $Ca^{++}$ channels and μ-/δ-opioid receptors in addition to the activation of 5HT1A, adenosine A2, glycine, GABA, and PPAR-γ receptors. CBD also may decrease nociceptive and inflammatory prostaglandins and produce an indirect increase in the level of endocannabinoids, anandamide and 2-AG, via suppressing COX2. TRPV1: transient receptor potential cation channel subfamily V member 1, GPR55: G protein-coupled receptor 55, NMDR: The N-methyl-d-aspartate receptor, COX2: cyclooxygenase, 5-HT: 5-hydroxytryptamine receptors, PPARγ: peroxisome proliferator-activated receptor gamma.

FIG. 8 shows the structures of several terpenoids present in a cannabis plant. As shown in FIG. 8, terpenoids have pharmacological activity including anti-inflammatory, anti-anxiety and analgesic effects. When administered with one or more cannabinoids, each terpenoid can produce a synergistic effect. Without being bound by any particular theory, it is believed that terpenes direct cannabinoids to the ECS and neural receptors, and subsequently the terpenes and cannabinoids interact with these receptors. These neural receptors can be found at different locations throughout the brain and affect the way the cannabinoids and terpenes interact within the ECS system. In one study, a FAAH inhibitor led to a 10× increase in anandamide (AEA) levels in many brain regions in mice.

Figure 9:
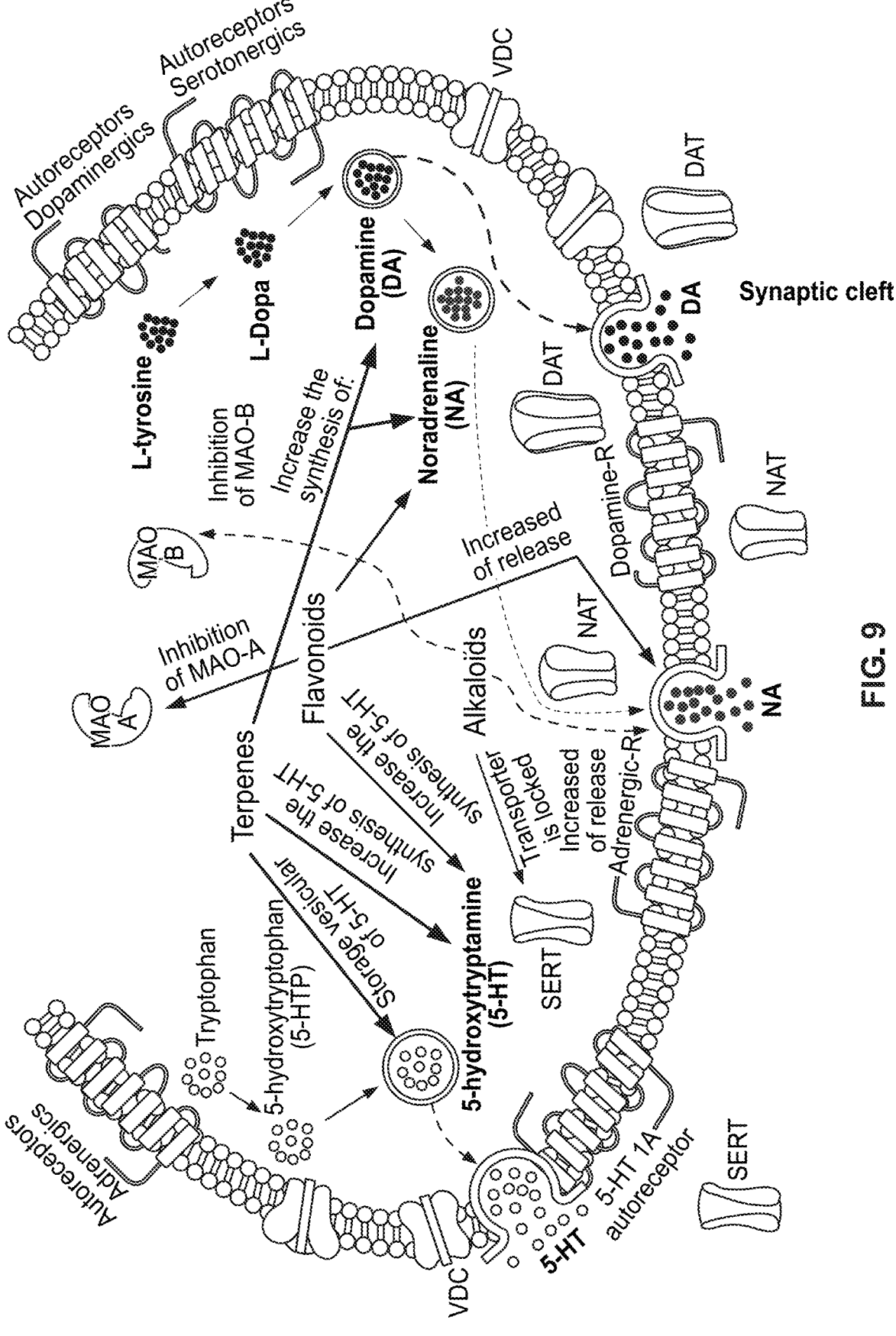
FIG. 9 is a diagram showing the effects of terpenes on the response of gamma-aminobutyric-acid (GABA) receptors allowing nerve cells to send and receive chemical messages.
Figure 9:
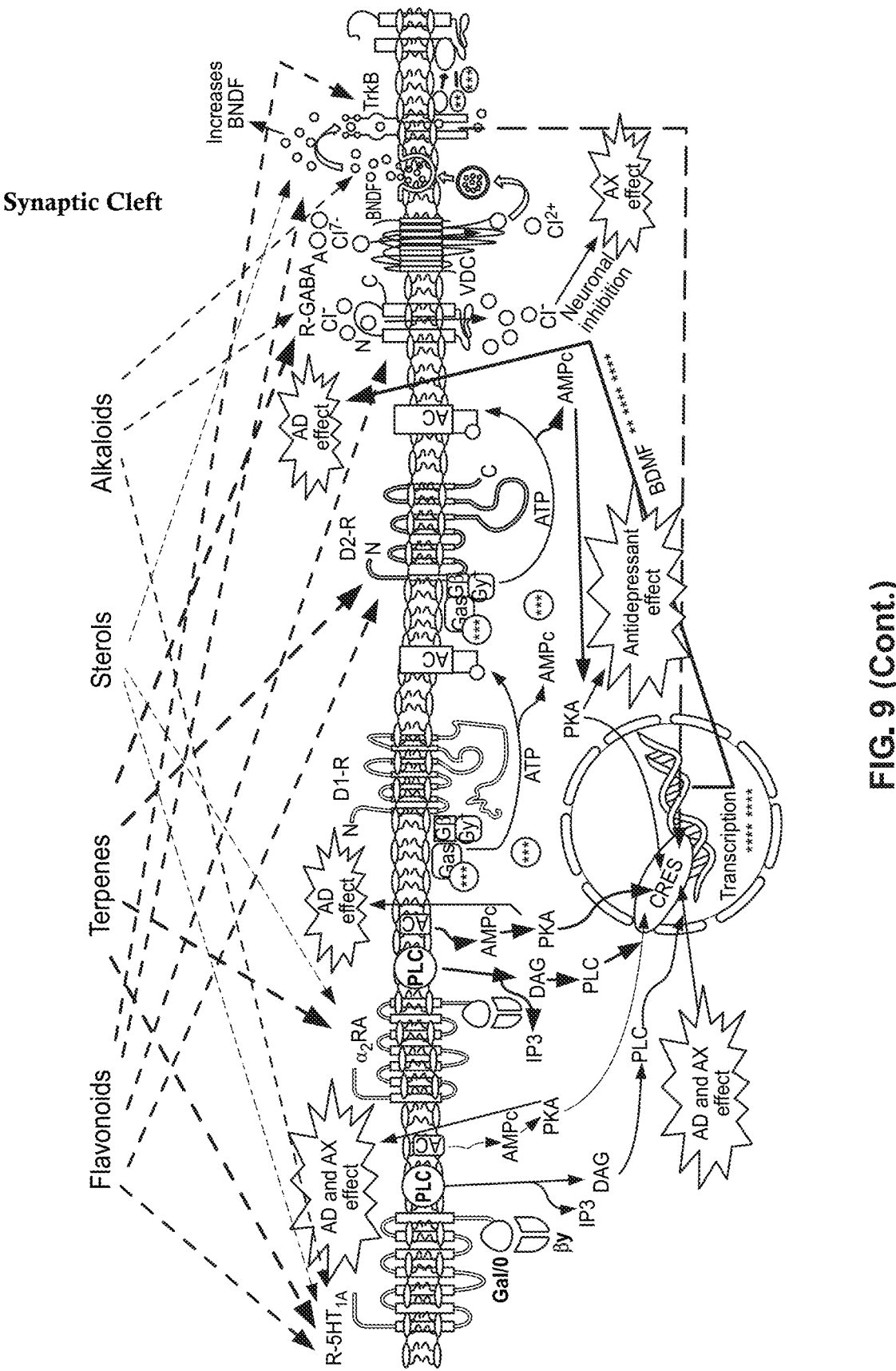

FIG. 9 is a diagram showing the effects of terpenes on the response of GABA receptors allowing nerve cells to send and receive chemical messages. Alpha (α) and β pinene also have been shown to increase the response of GABA receptors, this allows the nerve cells to better send and receive chemical messages. As shown in FIG. 9, the synaptic cleft is the space between two neurons across which the impulse is transmitted by a neurotransmitter. The neuron that transmits the signals are known as presynaptic neurons and the neurons that receive the signal are known as postsynaptic neurons. The interaction of terpenes with GABA, serotonin (5-HT2A), adenosine and dopamine receptors. Terpenes interact with GABA, serotonin (5-HT2A), adenosine and dopamine receptors, and work together to create antidepressant and anti-anxiety (AX) like effects without the negative side effects. Dosage forms according to embodiments herein similarly contain terpenes and cannabinoids that interact with the GABA, serotonin, adenosine and dopamine receptors within the ECS system.

Figure 10:
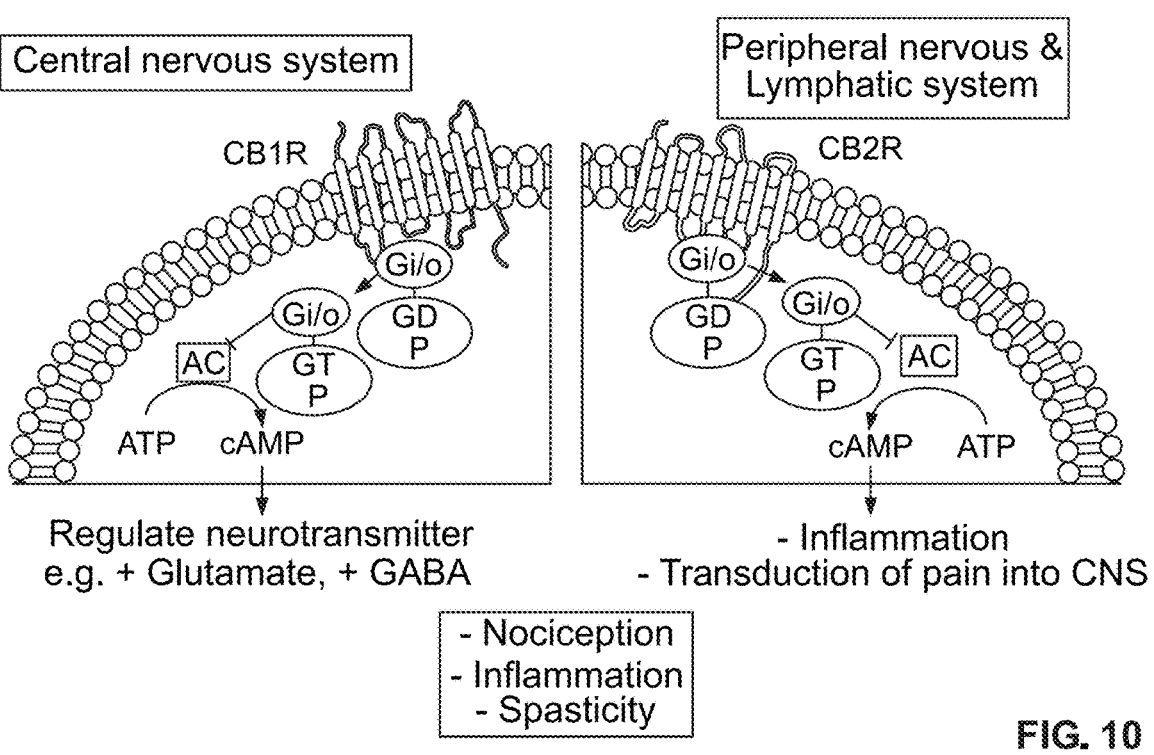
FIG. 10 is a diagram showing a possible anti-nociceptive and anti-inflammatory mechanism of cannabinoid receptors.

FIG. 10 is a diagram showing a possible anti-nociceptive and anti-inflammatory mechanism of cannabinoid receptors. Studies have shown that phytocannabinoids mediate their pharmacological actions through binding to CB1 and CB2 receptors and via regulation of the production and the degradation of endogenous endocannabinoids. The activation of the CB1 receptors centrally modulates nociceptive thresholds and produces multiple biological effects by regulating the balance between excitatory and inhibitory neurotransmitters such as glutamate and GABA, respectively. The activation of CB2 receptors peripherally suppresses the release of inflammatory mediators by cells located adjacent to nociceptive nerve terminals and blocks the transduction of pain signals into the CNS. See FIG. 10 (CB1R: cannabinoid receptor type 1, CB2R: cannabinoid receptor type 1, Gi/o: $G_i$ alpha subunit of G protein-coupled receptors, GDP: guanosine diphosphate, GTP: guanosine triphosphate, AC: adenylyl cyclase, ATP: Adenosine triphosphate, cAMP: cyclic-adenosine monophosphate. + indicates activates. – indicates inhibits).

CB2 receptors contribute to analgesia through suppressing the release of inflammatory mediators by cells located adjacent to nociceptive nerve terminals. Additionally, activation of peripheral CB2 receptors blocks transduction of pain signals into the CNS. Because CB2 receptors are expressed in several inflammatory cell and immunocompetent cell types, it is believed that activation of peripheral CB2 receptors may contribute to analgesic effect in conditions of inflammatory hyperalgesia and neuropathic pain such as multiple sclerosis. Without being bound by any particular theory, it is believed that cannabinoid-based pharmacotherapies are effective to reduce pain relating to multiple sclerosis.

Figure 11:
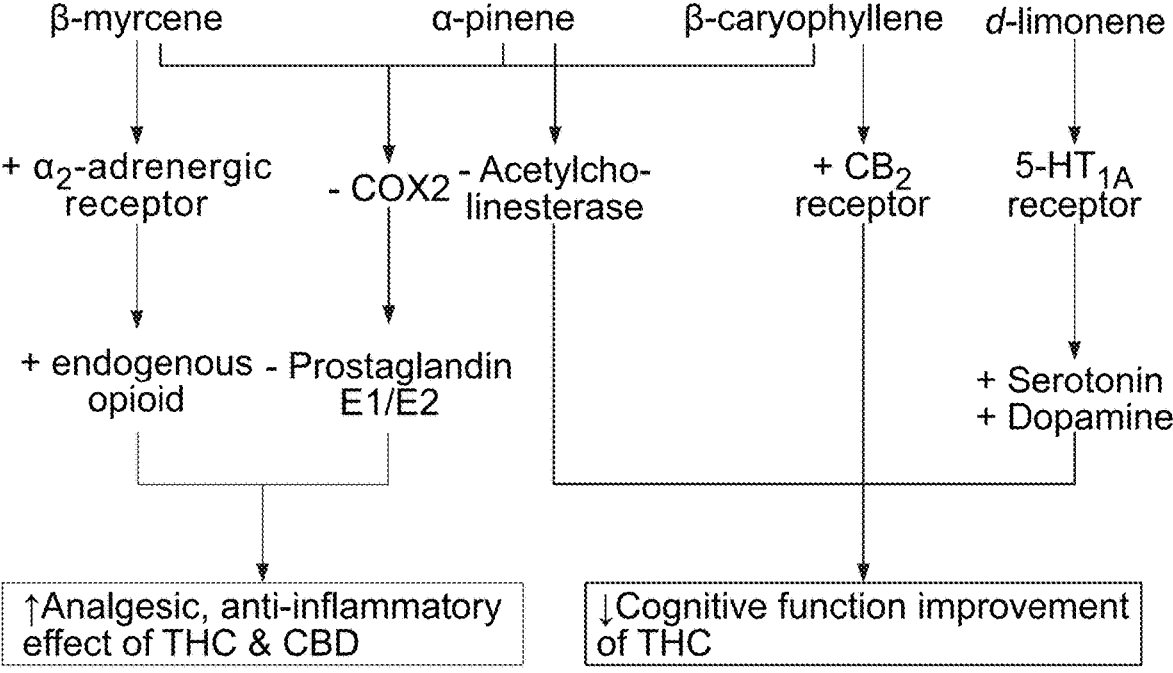
FIG. 11 is a diagram showing the effect of terpenes on acetylcholinesterase (AChE) enzymes and inflammation.

FIG. 11 is a diagram showing the effect of terpenes on AChE enzymes and inflammation. Much like linalool and BCP inhibit FAAH and fatty acid-binding proteins (FABP) to instigate brain recovery/health, α and β pinene terpenes can inhibit AChE enzymes and help with inflammation. Alpha (α)-pinene also has protective cell properties against oxidative stress, inflammation and neuronal damage. In addition, α-pinene inhibits inflammatory signaling pathways in immune cells and is shown to have antioxidant and anti-inflammatory effects in the hippocampus, cortex and striatum. Alpha (α)-pinene and α-humulene, alone and in combination, have been shown to prevent oxidative stress and astrocyte cell death. Essential Oil from a lemon containing α-pinene, β-pinene, limonene, linalool and BCP has been shown to have metal chelating capacity, inhibits lipid peroxidation and inhibits AChE and butyrylcholinesterase (BChE). All of these properties have therapeutic applications for neurodegenerative disorders. Alpha (α)-pinene inhalation has been shown to induce antidepressant and anti-anxiolytic effects. These effects were associated with increased dopamine in the hippocampus and striatum. Studies show increased mitochondrial function in the hippocampus and prefrontal cortex in rodents. Additionally, linalool and BCP are known to interact with serotonin receptors.

Dosage forms and compositions containing the described cannabis component according to embodiments herein are suitable for treating a variety of diseases and/or disorders including pain management. Phytol and Trans-Nerolidol are known to have anti-nociceptive properties. CBD also has anti-nociceptive properties. Phytol has been shown to promote antinociceptive effects that do not impair judgement. Studies have also shown phytol has antioxidant properties against free radicals. Trans-Nerolidol has a variety of pharmaceutical and biological properties such as anti-microbial, anti-parasitic, anti-biofilm, antioxidant, anti-inflammatory, anti-ulcer, skin penetration enhancer, insect repellent and anti-cancer properties. Trans-Nerolidol has been used to sensitize infectious bacteria and when combined with antibiotics can be a more effective treatment.

Antidepressant drugs act by reducing inflammation and opening up neural pathways in damaged parts of the brain. They also allow a person's thought process to focus on the positive versus negative, which helps promote brain health. Without being bound by any particular theory, it is believed that dosage forms and compositions comprising the cannabis component according to embodiments herein function in a similar manner through interactions of cannabinoids and terpenes within the ECS. The terpenes present in the dosage forms and compositions as described herein send cannabinoids to the proper neuro receptors as well as interact with the receptors themselves, providing euphoric and positive thoughts. The terpenes and cannabinoids support the ECS system and are suitable for treating depression, anxiety, PTSD, and other neurological disorders.

Cannabinoids (e.g., THC) and terpenes provide various therapeutic benefits. Not only can the cannabinoids and terpenes in the dosage forms and compositions as described herein function independently of each other, but they can also create a synergistic effect in treating the diseases and disorders described herein. Not all cannabis plants have pharmaceutical applications, but within the *Cannabis* L *sativa* family, there are plants such as those according to embodiments having novel and unique chemotypes for pharmaceutical applications.

The concept of breeding in the cannabis industry as it stands now is to continuously produce complex poly hybrids from the same genetic pool. This has led to a muddling of the therapeutic and pharmacological effects of most modern commercial varieties. The majority of cannabis varieties in the market are extremely incestuous and have not been bred in the classical agricultural sense. The industry uses "cuts," asexually propagated plants as the main means of experiencing, trading, and breeding. This limits the available genetic diversity and ensures the chemo typical expressions are locked in inbred depression. Because of prohibition, the need for fast flowering varieties that growers could get in and out of the door before police interception pushed longer flowering Narrow Leaf Drug (NLD) varieties out of the market. A small segment of growers hybridized the faster flower Wide Leaf Drug (WLD) varieties with NLD varieties, mostly hash plants from the Middle East in an attempt to preserve some of the traits they were targeting. Over the years, most of these plants have been selected and bred towards the WLD variety side, faster flowering, denser floral formations, high THC/CBD/Terpene chemotype but the plants have lost their novel effects. A small group of home growers and passionate cultivators around the world have kept a pool of these special genetics alive. A completely separate gene pool from today's commercial market entirely.

Novel and interesting chemotypes can still be found in cannabis plant such as those according to embodiments herein. Therapeutic *Cannabis sativa* plants can be found in the equatorial and subequatorial regions and have remained separate from modern industry. They can also be found in unique wild varieties that have not been bred using modern varieties. The variability and versatility of *Cannabis L. sativa* chemotypes provide new pathways for treatment of neurological and physiological diseases and/or disorders.

Without being bound by any particular theory, it is believed that the interaction of a UNIQUE FLOWER ORIGINAL HAZE chemotype contained within compositions and/or components according to embodiments herein with the ECS system, provides inter alia antidepressant and anti-anxiety effects in the subject. As such, dosage forms and compositions as described herein can be a useful treatment for various diseases and/or disorders that are affected by the ECS. Terpenes in the dosage forms and compositions according to embodiments herein, such as linalool and BCP, are FAAH inhibitors or inhibit their precursors, FABP. Tetrahydrocannabinol (THC) and Cannabidiol (CBD) both bind to FABP's, while CBD inhibits FAAH and prevents degradation of AEA and 2-AG by the FAAH, which supports the ECS.

Compositions and Components

Disclosed herein according to various embodiments are compositions and/or components. In one or more embodiments, the compositions and/or components can include plant material or derivatives thereof from The UNIQUE FLOWER ORIGINAL HAZE cultivar and/or having The UNIQUE FLOWER ORIGINAL HAZE chemotype. In various embodiments, the compositions can include ingredients that together form a profile that is representative of the chemotype.

In one or more embodiments, compositions as described herein include at least one cannabinoid. Suitable cannabinoids include, but are not limited to tetrahydrocannabinol (THC), $\Delta^9$-tetrahydrocannabinol ($\Delta^9$-THC, cannabidiol (CBD), tetrahydrocannabinolic acid (THCa), $\Delta^9$-tetrahydrocannabivarin (THCV), cannabidiolic acid (CBDa), cannabidivarin (CBDV), cannabinol (CBN), cannabigerolic acid (CBGa), cannabigerol (CBG), cannabichromene (CBC), a prodrug thereof, a pharmaceutically acceptable salt thereof or combinations of any two or more of the foregoing. The cannabinoid can be contained within an ingredient of the composition, the ingredient selected from plant material (e.g., plant parts, flowers, etc.), a plant derivative (e.g., extracts, oils, dried and ground parts, etc.), an isolated ingredient (e.g., THC powder, CBD powder, THC oil, CBD extract), a synthetic ingredient, a blend with other cannabinoids and/or ingredients in any form, or in combination thereof. In some embodiments, the compositions contain both THC and CBD. As discussed above, THC and CBD provide a therapeutic effect when administered for treating numerous diseases and/or disorders as described herein. Each individual cannabinoid or all cannabinoids combined may be present in the composition in an amount of about 0.001 wt % to about 99.99 wt %, or any individual value or sub-rang within this range.

According to various embodiments, compositions include, but are not limited to, based on the total weight of the composition, tetrahydrocannabinol (THC) in an amount of about 1 wt % to about 60 wt %, about 10 wt % to about 25 wt %, about 1 wt % to about 30 wt %, about 5 wt % to about 27 wt %, about 15 wt % to about 20 wt %, or any individual value or sub-range within these ranges. The composition may alternatively or additionally include cannabidiol (CBD) in an amount of about 0.001 wt % to about 60 wt %, about 0.001 wt % to about 50 wt %, about 0.001 wt % to about 25 wt %, about 0.001 wt % to about 10 wt %, about 0.001 wt % to about 1.0 wt %, about 0.01 wt % to about 0.5 wt %, about 0.1 wt % to about 0.4 wt %, or any individual value or sub-range within these ranges. Without being bound by any particular theory, it is believed that in or more embodiments, when THC and CBD are present together in the compositions, the combination can provide a synergistic effect in treating diseases and/or disorders (e.g., pain, anxiety, inflammation, epilepsy, cancer, fungal infection, etc.) according to embodiments herein. It is believed that CBD can reduce certain side effects of THC including anxiety, hunger and sedation.

In some embodiments, the compositions include or further include a particular THC or CBD cannabinoid and/or a cannabinoid other than THC or CBD. In various embodiments, the compositions include, but are not limited to, based on the total weight of the composition, at least one of: about 5 wt % to about 30 wt %, about 10 wt % to about 25 wt % or about 15 wt % to about 20 wt % Tetrahydrocannabinolic acid (THCa), about 0.1 wt % to about 10 wt %, about 0.5 wt % to about 5 wt % or about 1 wt % to about 2 wt % Δ⁹-tetrahydrocannabinol (Δ⁹-THC), about 0 wt % to about 1 wt % (THCV), about 5 wt % to about 30 wt %, about 10 wt % to about 25 wt % or about 15 wt % to about 20 wt % Cannabidiolic acid (CBDa), about 5 wt % to about 30 wt %, about 10 wt % to about 25 wt % or about 15 wt % to about 20 wt % Cannabidiol (CBD), about 5 wt % to about 30 wt %, about 10 wt % to about 25 wt % or about 15 wt % to about 20 wt % Cannabidivarin (CBDV), about 5 wt % to about 30 wt %, about 10 wt % to about 25 wt % or about 15 wt % to about 20 wt % Cannabinol (CBN), about 5 wt % to about 30 wt %, about 10 wt % to about 25 wt % or about 15 wt % to about 20 wt % Cannabigerolic Acid (CBGa), about 5 wt % to about 30 wt %, about 10 wt % to about 25 wt % or about 15 wt % to about 20 wt % Cannabigerol (CBG), about 5 wt % to about 30 wt %, about 10 wt % to about 25 wt % or about 15 wt % to about 20 wt % Cannabichromene (CBC), or any individual value or subrange within these ranges and/or a prodrug of any of the foregoing, a pharmaceutically acceptable salt of any of the foregoing or combinations of combinations of the foregoing.

Compositions according to embodiments herein can include or further include one or more terpenes, for example, at least one, at least two, at least three, or more terpenes. The one or more terpenes, alone or in combination with the other ingredients in the composition, are suitable to provide the above-mentioned effects within a subject's body following administration. In one or more embodiments, the compositions include about 0.001 wt % to about 50 wt % or about 0.01 wt % to about 25 wt % of the one or more terpenes, or any individual value or sub-range within this range.

The one or more terpenes can include β-Myrcene. Generally, it has been understood that the administration of β-Myrcene in the amount of 0.5 mg/g or more produces a heavy, narcotic, "couch lock" effect in a subject. However, the inventors discovered that compositions and/or components containing a corresponding high level of β-Myrcene, for example, about 8 mg/g or more provides antidepressant and/or antianxiety effects. In various embodiments, the compositions include, based on the total weight of the composition, about 0.01 wt % to about 5 wt % β-Myrcene, or any individual value or sub-range within this range. According to one or more embodiments, the composition includes at least about 1 mg/g β-Myrcene, at least about 2 mg/g β-Myrcene, at least about 3 mg/g β-Myrcene, at least about 4 mg/g β-Myrcene, at least about 5 mg/g β-Myrcene, at least about 8 mg/g β-Myrcene, or at least about 10 mg/g β-Myrcene. In some embodiments, the composition includes, based on the total weight of the composition, at least about 1 mg/g to about 15 mg/g β-Myrcene, about 2 mg/g to about 14 mg/g β-Myrcene, about 5 mg/g to about 10 mg/g β-Myrcene, about 6 mg/g to about 8 mg/g β-Myrcene, or any individual value or sub-range within these ranges.

Without being bound by any particular theory, it is believed that administration of compositions including a combination of the one or more terpenes (e.g., β-Myrcene)

and cannabinoids as described above (e.g., THC and CBD) can be used by the ECS system to provide beneficial effects to the subject. For example, β-Myrcene can be utilized by the ECS system in a variety of ways. β-Myrcene is a significant contributor to intracellular Ca²⁺ influxes by acting on transient receptor potential cation channel subfamily V member 1 (TRPV1) receptors, which increases the amount of AEA available (AEA is a TRPV1 activator). In the nervous system, TRPV1 receptors are involved in the transmission and modulation of pain. These interactions can produce antidepressant and antianxiety effects in a subject by increasing the amount of AEA concentrated in the brain and by reducing pain in the nervous system. β-Myrcene also reduces inflammation by blocking prostaglandins, similar to aspirin and ibuprofen. According to one or more embodiments, compositions can include plant material or an extract of plant material from the UNIQUE FLOWER ORIGINAL HAZE cannabis plant that contain a combination of one or more cannabinoids and one or more terpenes.

The cannabis plant can include one or more phenotype comprising a long flowering period, narrow leaves, looser floral formations, laxly branched growth form, higher resistance to insects as compared to fast-flowering varieties of *Cannabis sativa*, higher resistance to disease as compared to fast-flowering varieties of *Cannabis sativa* and/or dense glandular trichomes. In some embodiments, the *Cannabis sativa* plant produces about 10 resin glands/mm² to about 60 resin glands/mm².

Additionally or alternatively, compositions as described herein can include, based on the total weight of the composition, about 0.001 wt % to about 25 wt %, about 0.01 wt % to about 5 wt % of Ocimene 2, or any individual value or sub-range within these ranges. According to one or more embodiments, the composition includes, based on the total weight of the composition, at least about 0.1 mg/g Ocimene 2, at least about 0.5 mg/g Ocimene 2, at least about 1 mg/g Ocimene 2, at least about 2 mg/g Ocimene 2, at least about 3 mg/g Ocimene 2, or at least about 5 mg/g Ocimene 2. In some embodiments, the composition includes, based on the total weight of the composition, about 0.1 mg/g to about 8 mg/g Ocimene 2, about 0.5 mg/g to about 7 mg/g Ocimene 2, about 1 mg/g to about 5 mg/g Ocimene 2, or any individual value or sub-range within these ranges.

According to various embodiments, the compositions can include or further include one or more terpenes besides β-Myrcene and Ocimene 2. For example, the composition can include or further include one or more of cis-β-Farnesene, β-Caryophyllene, α-Pinene, (−)-β-Pinene, Limonene, α-Humulene, Linalool, Limonene, trans-Phytol, Terpinolene, a prodrug thereof, a pharmaceutically acceptable salt thereof and combinations of any two or more thereof. According to one or more embodiments, compositions can include or further include β-Caryophyllene and/or Linalool. BCP and linalool target FAAH and FABP in different parts of the body. Notably, lavender essential oil comprised of (about 1 wt % to about 50 wt %, or 36 wt %) linalyl acetate, (about 1 wt % to about 50 wt %, or 35.3 wt %) linalool and (about 0.1 wt % to about 20 wt %, or about 3.4%) BCP, can inhibit FAAH degradation enzymes and monoacylglycerol lipase (MAGL). 2-AG is degraded by MAGLs and AEA is degraded by FAAH enzymes, and the linalool and β-Caryophyllene can inhibit such degradation. When compositions according to embodiments herein are administered (e.g., by inhalation, ingestion etc.), the cannabinoids and terpenes inhibit FAAH and FABP to increase and prolong AEA and 2-AG production. A boost in Ca²⁺ levels also lead to increased AEA and 2-AG production in the brain.

As discussed herein, terpenes bind to CB2 receptors. Without being bound by any particular theory, compositions and/or components according to embodiments herein having the cannabinoids and terpene profile not only direct the cannabinoids to the proper neuroreceptors, but also interact with the ECS system and bind to suitable receptors themselves. BCP binds to CB2 receptors. The Japanese practice of forest bathing (walking through the pines) has been shown to relax your mind and reduce stress. By walking through the forest and inhaling the pine chemotype, essentially aroma therapy, engages a person's ECS system through the use of terpenes. Compositions and/or components according to embodiments herein can include α-Pinene, Limonene, and β-Myrcene that engage the ECS system.

The terpene α-humulene has marked anti-inflammatory properties when administered (e.g., orally or by aerosol) for airway inflammation resulting from allergies. Alpha (α)-humulene also has another therapeutic property that allows it to slow down eosinophil migration to inflammation sites. Leukotrienes, prostaglandins (PG), and platelet activating factor (PAF) are all involved in eosinophil influx and activation. Alpha (α)-humulene reduces eosinophil influx into the bronchoalveolar lavage fluid (BALF) and lung tissue when given preventatively or therapeutically. Compositions and/or components containing α-humulene (e.g., from The Unique Flower Original Haze) according to embodiments herein, when administered to a subject via pyrolysis and/or inhalation, causes the smoke to feel smooth. Limonene has been shown to prevent bronchial obstruction and reduce peribronchial inflammatory cell infiltration when inhaled. Limonene also protects the lungs from endo and exogenous ozone and oxidants and possesses bioactivities such as antitumor, antiviral, anti-inflammatory and antibacterial agents.

Ocimene and cis-β-Farnesene provide Acetylcholinesterase (AChE) inhibitory activity. AChE is an enzyme that functions by breaking down neurotransmitters. Sesquiterpenes such as Farnesene exert influence on Alzheimer's disease (AD) by targeting-amyloid (αβ) plaque, neuron excitability, and oxidative stress. This demonstrates the healing capacity of the terpenes on neurological degenerative disorders such as depression and anxiety.

Compositions according to embodiments herein can include α-pinene in an amount of, based on the total weight of the composition, at least about 0.01 wt %, at least about 0.1 wt %, at least about 0.5 wt %, at least about 1.0 wt %, at least about 5.0 wt %, or at least about 10 wt %. In one or more embodiments, the compositions include α-pinene in an amount of, based on the total weight of the composition, about 0.01 wt % to about 10 wt %, or any individual value or sub-range within this range. An α-pinene metabolite, (S)-cis-verbenol, increases intracellular calcium influx. Intracellular calcium ion ($Ca^{2+}$) movement and/or activation of G-protein-coupled receptors initiates AEA production.

Compositions according to one or more embodiments herein can include one or more of the aforementioned terpenes, based on the total weight of the composition, in an amount of about 0.001 wt % to about 25 wt %, or about 0.001 wt % to about 0.25 wt %, or any individual value or sub-range within these ranges. According to one or more embodiments, the composition includes or further includes each of the one or more of the aforementioned terpenes, based on the total weight of the composition, in an amount of at least about 0.005 mg/g, at least about 0.006 mg/g, at least about 0.008 mg/g, at least about 0.01 mg/g, at least about 0.02 mg/g, at least about 0.03 mg/g, at least about 0.04 mg/g, at least about 0.05 mg/g, at least about 0.06 mg/g, at least about 0.1 mg/g, at least about 0.2 mg/g, or at least about 0.25 mg/g. In some embodiments, the composition includes one or more of the aforementioned terpenes, based on the total weight of the composition, in an amount of at least about 0.005 mg/g to about 0.25 mg/g, about 0.008 mg/g to about 0.2 mg/g, about 0.01 mg/g to about 0.1 mg/g, or any individual value or sub-range within these ranges.

According to various embodiments, the composition can include, based on the total weight of the composition, at least one of: about 0.01 wt % to about 1.0 wt % cis-β-Farnesene, about 0.01 wt % to about 1.0 wt % β-Caryophyllene, about 0.005 wt % to about 0.5 wt % α-Pinene, about 0.001 wt % to about 0.1 wt % α-Humulene, about 0.001 wt % to about 0.1 wt % Linalool, about 0.001 wt % to about 0.1 wt % Limonene, about 0.01 wt % to about 1.0 wt % trans-Phytol, about 0.01 wt % to about 1.0 wt % Terpinolene, about 0.01 wt % to about 1.0 wt % (–)-β-Pinene, or any individual value or sub-range within these ranges. Compositions according to embodiments herein can be in any suitable form for incorporation into dosage forms and/or administration to a subject. Suitable forms include, but are not limited to, a powder, oil, liquid, emulsion, slurry, cream, lotion, dentifrice, gum, food product, supplement, alcohol, smoking device, inhalation device, adult use product, extractant or combinations thereof.

Further disclosed herein are components containing at least one cannabinoid. Components can be in the form of dried plant material, a plant extract, a plant oil, a synthetic cannabinoid, an isolated cannabinoid, a synthetic terpene, an isolated terpene, a synthetic flavanol, an isolated flavanol, a concentrate, or combinations thereof. Components can be combined with other ingredients (e.g., actives, excipients, etc.) to form a composition and/or dosage form.

In one or more embodiments, components as described herein include at least one cannabinoid. Suitable cannabinoids include, but are not limited to tetrahydrocannabinol (THC), $\Delta^9$-tetrahydrocannabinol ($\Delta^9$-THC, cannabidiol (CBD), tetrahydrocannabinolic acid (THCa), $\Delta^9$-tetrahydrocannabivarin (THCV), cannabidiolic acid (CBDa), cannabidivarin (CBDV), cannabinol (CBN), cannabigerolic acid (CBGa), cannabigerol (CBG), cannabichromene (CBC), a prodrug thereof, a pharmaceutically acceptable salt thereof or combinations of any two or more of the foregoing. The cannabinoid can be present in plant material (e.g., plant parts, flowers, etc.), a plant derivative (e.g., extracts, oils, dried and ground parts, etc.), an isolate (e.g., THC powder, CBD powder, THC oil, CBD extract), a synthetic ingredient, a blend of ingredients in any form, or in combinations thereof. In some embodiments, the component contains both THC and CBD.

According to various embodiments, each component can include, but is not limited to, based on the total weight of the component, tetrahydrocannabinol (THC) in an amount of about 10 wt % to about 100 wt %, about 1 wt % to about 95 wt %, about 5 wt % to about 80 wt %, about 15 wt % to about 50 wt %, or any individual value or sub-range within these ranges. The component may alternatively or additionally include cannabidiol (CBD) in an amount of about 0.001 wt % to about 100 wt %, about 0.01 wt % to about 95 wt %, about 0.05 wt % to about 50 wt %, about 0.1 wt % to about 0.4 wt %, or any individual value or sub-range within these ranges. Without being bound by any particular theory, it is believed that in or more embodiments, when a component containing both THC and CBD is administered to a subject (e.g., via a composition or dosage form), the combination can provide a synergistic effect in treating diseases and/or disorders (e.g., pain, anxiety, inflammation, epilepsy, cancer, fungal infection, etc.) according to embodiments herein.

In some embodiments, the component includes or further includes a particular THC or CBD cannabinoid and/or a cannabinoid other than THC or CBD. In various embodiments, the component can include, but is not limited to, based on the total weight of the component, at least one of: about 5 wt % to about 100 wt %, about 10 wt % to about 95 wt % or about 15 wt % to about 50 wt %, about 20 wt % to about 99 wt % Tetrahydrocannabinolic acid (THCa), about 0.1 wt % to about 100 wt %, about 0.5 wt % to about 95 wt %, about 1 wt % to about 50 wt %, about 5.0 wt % to about 25 wt % Δ⁹-tetrahydrocannabinol (Δ⁹-THC), about 0.001 wt % to about 1 wt % (THCV), about 5 wt % to about 100 wt %, about 10 wt % to about 95 wt % or about 15 wt % to about 50 wt %, about 5.0 wt % to about 25 wt % Cannabidiolic acid (CBDa), about 5 wt % to about 100 wt %, about 10 wt % to about 95 wt % or about 15 wt % to about 50 wt %, about 5.0 wt % to about 25 wt % Cannabidiol (CBD), about 5 wt % to about 100 wt %, about 10 wt % to about 95 wt % or about 15 wt % to about 50 wt %, about 5.0 wt % to about 25 wt % Cannabidivarin (CBDV), about 5 wt % to about 100 wt %, about 10 wt % to about 95 wt % or about 15 wt % to about 50 wt %, about 5.0 wt % to about 25 wt % Cannabinol (CBN), about 5 wt % to about 100 wt %, about 10 wt % to about 95 wt % or about 15 wt % to about 50 wt %, about 5.0 wt % to about 25 wt % Cannabigerolic Acid (CBGa), about 5 wt % to about 100 wt %, about 10 wt % to about 95 wt % or about 15 wt % to about 50 wt %, about 5.0 wt % to about 25 wt % Cannabigerol (CBG), about 5 wt % to about 100 wt %, about 10 wt % to about 95 wt % or about 15 wt % to about 50 wt %, about 5.0 wt % to about 25 wt % Cannabichromene (CBC), or any individual value or sub-range within these ranges and/or a prodrug of any of the foregoing, a pharmaceutically acceptable salt of any of the foregoing or combinations of combinations of the foregoing.

Components according to embodiments herein can include or further include one or more terpenes, for example, at least one, at least two, at least three, or more terpenes. The one or more terpenes, alone or in combination, are suitable to provide the above-mentioned effects within a subject's following administration. In one or more embodiments, the component includes about 0.01 wt % to about 100 wt % of the one or more terpenes, or any individual value or sub-range within this range.

The one or more terpenes can include β-Myrcene. In various embodiments, the component includes, based on the total weight of the component, about 0.01 wt % to about 100 wt % β-Myrcene, or any individual value or sub-range within this range. According to one or more embodiments, the component includes, based on the total weight of the component, at least about 1 mg/g β-Myrcene, at least about 2 mg/g β-Myrcene, at least about 3 mg/g β-Myrcene, at least about 4 mg/g β-Myrcene, at least about 5 mg/g β-Myrcene, at least about 8 mg/g β-Myrcene, at least about 10 mg/g β-Myrcene, at least about 50 mg/g β-Myrcene, at least about 100 mg/g β-Myrcene, or at least about 1000 mg/g β-Myrcene. In some embodiments, the component includes, based on the total weight of the component, at least about 1 mg/g to about 1000 mg/g β-Myrcene, about 2 mg/g to about 500 mg/g β-Myrcene, about 5 mg/g to about 100 mg/g β-Myrcene, about 6 mg/g to about 8 mg/g β-Myrcene, or any individual value or sub-range within these ranges.

Additionally or alternatively, components as described herein can include, based on the total weight of the component, about 0.01 wt % to about 100 wt % of Ocimene 2, or any individual value or sub-range within this range. According to one or more embodiments, the component includes, based on the total weight of the component, at least about 0.1 mg/g Ocimene 2, at least about 0.5 mg/g Ocimene 2, at least about 1 mg/g Ocimene 2, at least about 2 mg/g Ocimene 2, at least about 3 mg/g Ocimene 2, at least about 5 mg/g Ocimene 2, at least about 25 mg/g Ocimene 2, at least about 50 mg/g Ocimene 2, at least about 100 mg/g Ocimene 2, or at least about 1000 mg/g Ocimene 2. In some embodiments, the component includes, based on the total weight of the component, about 0.1 mg/g to about 1000 mg/g Ocimene 2, about 0.5 mg/g to about 500 mg/g Ocimene 2, about 1 mg/g to about 100 mg/g Ocimene 2, or any individual value or sub-range within these ranges.

According to various embodiments, the components can include or further include one or more terpenes besides β-Myrcene and Ocimene 2. For example, the component can include or further include one or more of cis-β-Farnesene, β-Caryophyllene, α-Pinene, (–)-β-Pinene, Limonene, α-Humulene, Linalool, Limonene, trans-Phytol, Terpinolene, a prodrug thereof, a pharmaceutically acceptable salt thereof and combinations of any two or more thereof. According to one or more embodiments, the component can include or further include β-Caryophyllene and/or Linalool. In one or more embodiments, the component is an essential oil containing one or more terpenes. Suitable essential oils containing terpenes include, but are not limited to, lavender essential oil (containing BCP and linalool), bergamot, carrot, fennel, lemon, neroli, orange and/or citrus essential oil (containing limonene), coriander, cypress, eucalyptus, pin, black pepper and/or oregano essential oil (containing pinene) and/or juniper, fir, spruce and/or pine essential oil (containing camphene). In various embodiments, the component is lavender essential oil containing BCP and linalool.

Components according to embodiments herein can include α-pinene in an amount of, based on the total weight of the component, at least about 0.01 wt %, at least about 0.1 wt %, at least about 0.5 wt %, at least about 1.0 wt %, at least about 5.0 wt %, at least about 10 wt %, at least about 15 wt %, at least about 20 wt %, at least about 25 wt %, at least about 50 wt %, or about 100 wt %. In one or more embodiments, the component includes α-pinene in an amount of, based on the total weight of the component, about 0.01 wt % to about 100 wt %, or any individual value or sub-range within this range.

Components according to one or more embodiments herein can include one or more of the aforementioned terpenes, based on the total weight of the component, in an amount of about 0.001 wt % to about 100 wt %, or any individual value or sub-range within this range. According to one or more embodiments, the component includes or further includes one or more of the aforementioned terpenes, based on the total weight of the component, in an amount of at least about 0.005 mg/g, at least about 0.01 mg/g, at least about 0.1 mg/g, at least about 1.0 mg/g, at least about 5 mg/g, at least 10 mg/g, at least about 25 mg/g, at least about 50 mg/g, at least about 100 mg/g, at least about 1000 mg/g, or any individual value or sub-range within these ranges. In some embodiments, the composition includes, based on the total weight of the composition, each of the one or more aforementioned terpenes, based on the total weight of the composition, in an amount of at least about 0.005 mg/g to about 0.25 mg/g, about 0.008 mg/g to about 0.2 mg/g, about 0.01 mg/g to about 0.1 mg/g, or any individual value or sub-range within these ranges.

According to various embodiments, the component includes, based on the total weight of the component, at least one of: about 0.01 wt % to about 1.0 wt % cis-β-Farnesene, about 0.01 wt % to about 1.0 wt % β-Caryophyllene, about 0.005 wt % to about 0.5 wt % α-Pinene, about 0.001 wt % to about 0.1 wt % α-Humulene, about 0.001 wt % to about 0.1 wt % Linalool, about 0.001 wt % to about 0.1 wt % Limonene, about 0.01 wt % to about 1.0 wt % trans-Phytol, about 0.01 wt % to about 1.0 wt % Terpinolene, and about 0.01 wt % to about 1.0 wt % (−)-β-Pinene. According to one or more embodiments, the component includes, based on the total weight of the component, about 10 wt % to about 25 wt % tetrahydrocannabinol (THC), about 0.001 wt % to about 1.0 wt % cannabidiol (CBD), about 0.01 wt % to about 5 wt % β-Myrcene, and about 0.01 wt % to about 5 wt % Ocimene 2, or any individual value or sub-range within these ranges.

Dosage Forms

Further disclosed herein are various embodiments of dosage forms containing compositions and/or components according to embodiments herein. The dosage form can be in any suitable form for administration to a subject. Suitable forms of administration include, but are not limited to oral, parenteral, inhalation, rectal, intravaginal, sublingual, intramuscular injection, transdermal, nasal, buccal, insufflation, or spinal anesthesia.

In various embodiments, the dosage form is a solid oral dosage form. In one or more embodiments, the solid oral dosage form is a tablet, a hard shell capsule, a soft shell capsule, a caplet, a sublingual tablet, a sublingual film, a buccal tablet, a buccal film, a gummy, a food product (e.g., chips, cookies, candies, chocolates, etc.), a matrix, particles, a spray, or combinations thereof. In one or more embodiments, the dosage form is a cigarette, joint, dried flower, liquid, beverage, alcoholic beverage, coffee, coffee grounds, or combinations thereof.

The dosage form can include plant material, for example, plant material from a UNIQUE FLOWER ORIGINAL HAZE cultivar of *Cannabis sativa*, ssp. *sativa*. The plant material can be in any suitable form for incorporation into a dosage form including, but not limited to, dried flowers, dried leaves, extracts, oils, derivatives thereof and/or combinations thereof. The plant material can be formed into a powder, granules, pellets, extrudates and/or liquids for combination with other ingredients to form the dosage form.

The dosage form can include at least one cannabinoid. Suitable cannabinoids include, but are not limited to THC, CBD, Tetrahydrocannabinolic acid (THCa), $\Delta^9$-tetrahydrocannabinol ($\Delta^9$-THC), $\Delta^9$-Tetrahydrocannabivarin (THCV), Cannabidiolic acid (CBDa), Cannabidiol (CBD), Cannabidivarin (CBDV), Cannabinol (CBN), Cannabigerolic Acid (CBGa), Cannabigerol (CBG), Cannabichromene (CBC), a prodrug thereof, a pharmaceutically acceptable salt thereof or combinations thereof. The at least one cannabinoid may be present in an amount of, based on the total weight of the dosage form, greater than 0 wt % to about 30 wt %, about 0.05 wt % to about 25 wt %, about 0.1 wt % to about 20 wt %, or about 1.0 wt % to about 18 wt % based on the total weight of the dosage form.

In some embodiments, the dosage form includes at least one of: about 5 wt % to about 30 wt %, about 10 wt % to about 25 wt % or about 15 wt % to about 20 wt % Tetrahydrocannabinolic acid (THCa), about 0.1 wt % to about 10 wt %, about 0.5 wt % to about 5 wt % or about 1 wt % to about 2 wt % $\Delta^9$-tetrahydrocannabinol ($\Delta^9$-THC), about 0 wt % to about 1 wt % (THCV), about 5 wt % to about 30 wt %, about 10 wt % to about 25 wt % or about 15 wt % to about 20 wt % Cannabidiolic acid (CBDa), about 5 wt % to about 30 wt %, about 10 wt % to about 25 wt % or about 15 wt % to about 20 wt % Cannabidiol (CBD), about 5 wt % to about 30 wt %, about 10 wt % to about 25 wt % or about 15 wt % to about 20 wt % Cannabidivarin (CBDV), about 5 wt % to about 30 wt %, about 10 wt % to about 25 wt % or about 15 wt % to about 20 wt % Cannabinol (CBN), about 5 wt % to about 30 wt %, about 10 wt % to about 25 wt % or about 15 wt % to about 20 wt % Cannabigerolic Acid (CBGa), about 5 wt % to about 30 wt %, about 10 wt % to about 25 wt % or about 15 wt % to about 20 wt % Cannabigerol (CBG), about 5 wt % to about 30 wt %, about 10 wt % to about 25 wt % or about 15 wt % to about 20 wt % Cannabichromene (CBC), or any individual value or sub-range within these ranges, a prodrug of any of the foregoing, a pharmaceutically acceptable salt of any of the foregoing or combinations of the foregoing.

Dosage forms according to embodiments herein can include THC, alone or in combination with CBD as described herein with respect to the above compositions and/or components. In some embodiments, the dosage form includes or further includes at least about 2 mg/g β-Myrcene, at least about 3 mg/g β-Myrcene, at least about 4 mg/g β-Myrcene, at least about 5 mg/g β-Myrcene or at least about 8 mg/g β-Myrcene. In various embodiments, the dosage form can include at least about 1 mg/g to about 15 mg/g β-Myrcene, about 2 mg/g to about 14 mg/g β-Myrcene, about 5 mg/g to about 10 mg/g β-Myrcene, about 6 mg/g to about 8 mg/g β-Myrcene, or any individual value or sub-range within these ranges.

Dosage forms described herein can further include one or more terpenes. Suitable terpenes include, but are not limited to, β-Myrcene, Ocimene 2, cis-β-Farnesene, β-Caryophyllene, α-Pinene, (−)-β-Pinene, Limonene, α-Humulene, Linalool, Limonene, trans-Phytol, Terpinolene, a prodrug thereof, a pharmaceutically acceptable salt thereof and combinations of any two or more thereof. According to one or more embodiments, the dosage form can include or further include β-Caryophyllene and/or Linalool. In various embodiments, the dosage form includes at least one of: about 0.01 wt % to about 1.0 wt % cis-β-Farnesene, about 0.01 wt % to about 1.0 wt % β-Caryophyllene, about 0.005 wt % to about 0.5 wt % α-Pinene, about 0.001 wt % to about 0.1 wt % α-Humulene, about 0.001 wt % to about 0.1 wt % Linalool, about 0.001 wt % to about 0.1 wt % Limonene, about 0.01 wt % to about 1.0 wt % trans-Phytol, about 0.01 wt % to about 1.0 wt % Terpinolene, or about 0.01 wt % to about 1.0 wt % (−)-β-Pinene based on the total weight of the cannabis component.

In one or more embodiments, the dosage form includes, based on the total weight of the dosage form, about 10 wt % to about 25 wt % tetrahydrocannabinol (THC); about 0.001 wt % to about 1.0 wt % cannabidiol (CBD); about 0.01 wt % to about 5 wt % β-Myrcene; and about 0.01 wt % to about 5 wt % Ocimene 2.

In one or more embodiments, the dosage forms can further include an excipient such as a pharmaceutically acceptable excipient. Suitable pharmaceutically acceptable excipients are described herein below.

Excipients

Compositions and dosage forms according to one or more embodiments herein can include at least one excipient, for example, a pharmaceutically acceptable excipient. Examples of possible excipients are described in the Handbook of Pharmaceutical Excipients, American Pharmaceutical Association (2012), which is incorporated by reference herein, as well as other applicable excipients. Suitable excipients include, but are not limited to, plasticizers, colorants, lubricants, thermal lubricants, antioxidants, buffering agents, disintegrants or granulating agents, binding agents, diluents, glidants, anti-adherents, sweeteners, chelating agents, granulating agents, bulking agents, flavorants, surfactants, solubilizers, stabilizers, hydrophilic polymers, hydrophobic polymers, waxes, lipophilic materials, absorption enhancers, preservative, absorbent, cross-linking agents, bioadhesive polymers, pore formers, osmotic agents, polycarboxylic acids, and combinations of any two or more of the foregoing.

Examples of suitable binding agents include, but are not limited to, cellulosic polymers (e.g., hydroxypropylmethylcellulose, hydroxypropylcellulose, hydroxyethylcellulose, etc.), polyethylene glycol, an acrylic polymer, an acrylic copolymer, a graft copolymer of polyvinyl alcohol and polyethylene glycol, a polyvinyl alcohol, alginic acid, sodium alginate, starch, pregelatinized starch, sucrose, guar gum, salts thereof, derivatives thereof and combinations thereof. Additional binders include, but are not limited to, natural or synthetic waxes, fatty alcohols (e.g., lauryl, myristyl, stearyl, cetyl or cetostearyl alcohol), fatty acids, including, but not limited to, fatty acid esters, fatty acid glycerides (e.g., mono-, di-, and tri-glycerides), hydrogenated fats, hydrocarbons, stearic acid, hydrophobic and hydrophilic materials having hydrocarbon backbones, acacia, tragacanth, sucrose, gelatin, glucose, cellulose materials (e.g., methylcellulose and sodium carboxymethylcellulose (e.g., Tylose™)), magnesium aluminum silicate, polysaccharide acids, bentonites, polyvinylpyrrolidone (povidone), polymethacrylates, and pregelatinized starch (such as National™ 1511 and Starch 1500). Suitable waxes include, for example, beeswax, glycowax, castor wax, carnauba wax and other wax-like substances. A "wax-like" substance is defined as any material which is normally solid at room temperature and has a melting point of from about 30° C. to about 100° C.

Additional examples of binders which may be used include, but are not limited to, digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. In certain embodiments, hydrocarbons having a melting point of between 25° C. and 90° C. may be included. Of the long-chain hydrocarbon binder materials, fatty (aliphatic) alcohols can be incorporated into the mixture according to certain embodiments.

Examples of suitable disintegrants include, but are not limited to, sodium starch glycolate, clays (such as Veegum™ HV), celluloses (such as purified cellulose, methylcellulose, sodium carboxymethylcellulose, and carboxymethylcellulose), cross-linked sodium carboxymethylcellulose, starch, cross-linked polyvinylpyrrolidone (e.g., crospovidone), alginates, corn starches and pre-gelatinized corn starches (such as National™ 1551 and National™ 1550), gums (such as agar, guar, locust bean, pectin, and tragacanth) and mixtures thereof. Disintegrants can be added at any suitable step during the preparation of the pharmaceutical compositions, such as prior to granulation or during a lubrication step prior to compression or encapsulation.

Suitable bulking agents include, but are not limited to, starches (e.g., corn starch), microcrystalline cellulose, lactose (e.g., lactose monohydrate), sucrose, dextrose, mannitol, calcium phosphate and dicalcium phosphate.

According to certain embodiments, the compositions may include a plasticizer. Plasticizers may interact with hydrophobic materials resulting in a lower viscosity of the mixture as compared to the mixture without the plasticizer when measured under the same conditions. Certain plasticizers may lower the glass transition temperature (Tg) of hydrophobic materials. Suitable plasticizers include, but are not limited to, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers may include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, acetyl triethyl citrate, tributyl citrate and allyl glycolate.

In at least one embodiment, the composition includes a glidant. A glidant is an excipient that improves the flow characteristics of a compressible powder such as tablet components or granules. Suitable glidants include, but are not limited to, silicon dioxide, colloidal silicon dioxide and the like.

Suitable diluents useful in compositions as described herein include, but are not limited to, lactose (e.g., lactose (anhydrous), lactose (spray dried), lactose monohydrate), starch (e.g., directly compressible starch), mannitol, sorbitol, dextrose monohydrate, microcrystalline cellulose, dibasic calcium phosphate dihydrate, sucrose-based diluents, confectioner's sugar, monobasic calcium sulfate monohydrate, calcium sulfate dihydrate, calcium lactate trihydrate granular, dextrates (e.g., Emdex™), dextrose (e.g., Cerelose™), inositol, hydrolyzed cereal solids such as the Maltrons™ and Mor-Rex™, amylose, powdered cellulose (e.g., Elcema™), calcium carbonate, glycine, bentonite, polyvinylpyrrolidone, and the like.

Suitable lubricants include, but are not limited to, glyceryl behenate (Compritol™ 888) metallic stearates (e.g., magnesium, calcium and sodium stearates), stearic acid, hydrogenated vegetable oils (e.g., Sterotex™), talc, waxes such as beeswax and carnauba wax, silica, fumed silica, colloidal silica, calcium stearate, long chain fatty alcohols, boric acid, sodium benzoate and sodium acetate, sodium chloride, DL-Leucine, polyethylene glycols (e.g., Carbowax™ 4000 and Carbowax™ 6000), sodium oleate, sodium benzoate, sodium acetate, sodium lauryl sulfate, sodium stearyl fumarate (Pruv™), magnesium lauryl sulfate, stearic acid, stearyl alcohol, mineral oil, paraffin, micro crystalline cellulose, glycerin, propylene glycol and combinations thereof.

Suitable anti-adherents include, but are not limited to, talc, cornstarch, colloidal silicone dioxide (Cab-O-Sil™), DL-Leucine, sodium lauryl sulfate, and metallic stearates.

Other excipients (such as colorants, flavorants and sweeteners) can be utilized in embodiments of the compositions where they impart little to no deleterious effect on the stability of the pharmaceutical composition.

In certain embodiments, the composition may include a film coat. The film coat may include, but is not limited to, hydroxypropylmethylcellulose, polyethylene glycol, polyvinyl alcohol or a mixture of any two or more thereof.

Methods of Preparation

This new cultivar was asexually reproduced via stem-cutting and cloning using two different methods. In the first, lateral shoots were cut at an internode leaving a 4-6" cutting that was then dipped into a rooting hormone, inserted into a Rapid Tooter plant starter cube, and placed into a clone dome for 8-14 days or until roots were visible. In the second, cuttings were taken and placed in plain water for at least 24 hours, then transplanted straight into soil. Both methods were performed by the inventors at the Unique Flower LLC facilities in Rainier, Oregon, with asexual clones grown in greenhouses at the Unique Flower LLC facilities in Rainier, Oregon. The stem cuttings resulting in asexual propagation were approximately 14 cm long and had multiple auxiliary meristems. These clones were allowed to root for 14 to 18 days prior to being introduced to large, raised beds. They were lightly fed with organic inputs and defoliated and pruned as necessary throughout their growing cycle. The clones were flowered in a light deprivation greenhouse with 315 Ceramic Metal Halides as supplemental lighting. The floral transition was initiated by switching to 11-hour days and 13-hour nights in the greenhouse. Flowering continued for 14-15 weeks until harvest, at which point morphological measurements were taken, samples were taken for chemical analysis, and yield was quantified.

Compositions, components and dosage forms according to various embodiments described herein can be prepared using any suitable method known to those of ordinary skill in the art. Such methods include, but are not limited to wet granulation, dry granulation, compression, extrusion, encapsulation, and any other suitable methods known to those of ordinary skill in the art to prepare compositions and dosage forms as described herein. According to embodiments, one or more components of the compositions or dosage forms can be prepared in a matrix in the form of particles, a powder, granules, beads, microspheres and combinations thereof. For example, in one embodiment, granules can be formed from at least one component and at least one component. The granules of each component can be combined into a matrix. Additional components can be added to the matrix as desired. In embodiments, the matrix can be compressed and shaped to form a tablet or a micro-tablet. In further embodiments, the matrix can be converted into an extrudable form and then extruded to form extrudates.

The granules can be formed by any procedure known to those of ordinary skill in the art. For example, the granules may be formed by wet granulation with water or dry granulation. In an embodiment of a wet granulation process, at least one stress buster component and at least one calming reliever component are weighed, sifted and mixed (excluding a lubricant), optionally with one or more excipient such as a bulking agent, filler, diluent and disintegrant, in a powder mixer. The components can be mixed using a planetary bowl mixer, ribbon/trough mixer, rotating drum mixer or high-speed mixer until a uniform powder mix (i.e., a matrix) is achieved. The mixing efficiency can be enhanced by the use of powders that have similar average particle size, although this is often not the case in many mixing operations.

Suitable diluents include, but are not limited to lactose, microcrystalline cellulose, starch, powdered sucrose, mannitol, fructose, sorbitol, calcium phosphate and calcium sulphate. Diluents are usually selected based on the manufacturer's experience with the material, its relative cost, and its compatibility with the drug and other excipients. Suitable disintegrants include, but are not limited to croscarmellose, sodium starch glycolate, sodium carboxymethylcellulose, polyvinylpyrrolidone (PVP), crospovidone, cation exchange resins, corn and potato starches, alginic acid and other materials that counteract the effect of binders and the physical forces of compression used in forming the tablets.

The wet granulation method can further include preparing a damp mass. In embodiments, the amount of water added during the wet granulation can be about 1.5 to about 5 times, or about 1.75 to about 3.5 times the dry weight of the matrix. The binder solution can be mixed with the powder mixture to form an adhesive mass, which can be granulated. The amount of binding agent used as well as the quantity of fluid required to form a damp and coherent mass is known to those of ordinary skill in the art. The resulting binder-powder mixture should compact when squeezed in the hand. The use of insufficient binder tends to poor adhesion, capping and soft tablets. Excessive binder solution yields hard tablets with slow disintegrating properties. Suitable granulating agents are solutions of povidone, an aqueous preparation of cornstarch, molasses, methylcellulose, hydroxypropyl methylcellulose, carboxymethylcellulose, glucose solution and microcrystalline cellulose. Suitable dry binders or nonaqueous solution can be used for substances that are adversely affected by aqueous solution. Colorants or flavoring agents can be added to the binding agent to prepare a granulation with an added feature.

The dampened powder can be wet screened into pellets or granules. The wet massed powder blend can be screened using a 6- to 12-mesh screen to prepare wet granules. This may be done by hand or with suitable equipment that prepares the granules by extrusion through perforations in the apparatus. The granules formed are spread evenly on trays and dried in an oven.

The screened moist granules are then dried in an oven at a controlled temperature not exceeding 55° C. to a consistent weight or constant moisture content. The drying temperature and the duration of drying process depend on the nature of the active component and the level of moisture required for the successful production of satisfactory tablets. Shelf or tray drier and fluidized-bed drier can be used for this purpose.

The dried granules are passed through a screen of smaller size than that used to prepare the moist granules. The size of the final granules is dependent on the size of the punches (and hence the final tablet size). Screens of 14- to 20-mesh size are generally used for this purpose.

After dry screening, the dried and screened granules can be separated into coarse and fine granules by shaking them on a 250-mesh sieve. An appropriate quantity of lubricant is passed through a 200-mesh sieve. This is mixed with the fine granules before the coarse granules are incorporated. The quantity of lubricant used varies from one formulation scientist to another but usually ranges from about 0.1% to 5% of the weight of the granulation.

Suitable lubricants for use in wet granulation include, but are not limited to magnesium stearate, calcium stearate, stearic acid, wax, hydrogenated vegetable oil, talc, and starch.

A suitable dry granulation process includes weighing formulation components in appropriate quantities. The excipients and active component(s) should be in finely divided form, otherwise, particle size reduction should be carried out.

The weighed formulation components are mixed in a powder mixer until a uniform powder mix is achieved. In embodiments, half the lubricant in the formula can be added at this stage to enhance powder flow during slugging and to prevent sticking of compressed powder on the die during precompression.

The mixed components can then be compressed into flat large tablets or pellets, referred to as precompression (a.k.a., slugging) and the compacts made in the process typically have a size of about 25 mm diameter by about 10-15 mm thick. Compression of mixed powders into slugs can be achieved by slugging technique or roller compaction. The pressure used to produce the slugs is usually less than that used in the final compression.

Following slugging, the slugs are broken into smaller pieces using a hammer mill or other conventional milling equipment. The milled slugs are screened to produce uniform granules. After screening, the remaining lubricant and other extragranular excipients such as disintegrant, glidant etc. as described herein, can be added to the granulation and mixed gently to achieve a uniform blend. The mixed granules can be compressed into tablets using either a single or rotary tablet press fitted with appropriate punches and dies. Similar to wet granulation, tablets manufactured by dry granulation method may be coated if the need arises. The disintegrant can be added to the weighed formulation at the beginning of the process (intragraular) or to the screened milled slugs (extragranular) and sometimes in both steps (intragranular-extragranular). The formed granules can then be compressed into tablets or micro-tablets.

In certain embodiments, matrices can be formed using a melt-granulation or melt-extrusion technique. Generally, melt-granulation techniques involve melting a normally solid binder material, e.g., a wax, and incorporating a powder therein. Other components can be added, for example, release modifying agents, diluents, lubricants, binders, granulating aids, colorants, flavorants and glidants that are conventional in the pharmaceutical art in amounts up to about 50% by weight of the particulate if desired. The quantities of these additional materials will be sufficient to provide the desired effect to the desired formulation.

According to embodiments, methods of preparing dosage forms as described herein can include a number of pharmaceutically acceptable preparation techniques (e.g., granulation, extrusion, compression, coating, encapsulation, etc. as discussed above) known to those of ordinary skill in the art. In embodiments, methods of preparation include granulating one or more components (e.g., at least one stress buster and at least one calming reliever) to form a matrix. Compressing (and optionally shaping) the matrix to form one or more micro-tablets using, for example, a tablet press. For example, the matrix can be compressed into tablets in a single rotary tablet press with a plurality of punch pairs. The punches can have a diameter of about 1 mm to about 10 mm.

Suitable techniques for extracting inter alia cannabinoids and terpenes from plants according to embodiments herein for use in dosage forms include, but are not limited to, dry sifting, hydrocarbon extraction, rosin press heat extraction, water extraction, synthesizing cannabinoids and adding terpenes, distillation, drying plant material, decarboxylation, alcohol extraction, oil and/or combinations thereof. Dry sifting techniques can include running dried cannabis flowers over sifting screens having various mesh sizes in order to separate resin heads from the flowers.

Hydrocarbon extraction techniques can include using butane hash oil or carbon dioxide ($CO_2$) extraction. Butane Hash Oil (BHO) is a solvent-based concentrate. This extract is made by using butane, a light hydrocarbon solvent, to strip away resin from cannabis plants. This process utilizes closed-loop extraction systems and methods involving a butane solvent collection vessel, an adsorbent or filtration column, a collection vessel, a pump and a condenser. Carbon dioxide extraction can produce a cannabis oil suitable for use in dosage forms and compositions according to embodiments herein. A high-pressure (i.e., supercritical) form of carbon dioxide is used as the solvent. This supercritical $CO_2$ solvent acts as a gas by filling in every nook and cranny of an extraction tube. Carbon dioxide also retains a liquid-like density that is powerful enough to wash away cannabinoids and terpene compounds. The supercritical $CO_2$ fluid can be passed over the raw material to strip away the valuable resinous trichomes. The compound is "tunable" so that the waxes and lipids aren't separated with cannabis oil.

Rosin press heat extraction utilizes a rosin press that uses only heat and pressure to separate cannabinoids and terpenes from the raw plant material. A rosin press uses heated plates to extract cannabis compounds. The plant material is commonly sorted into special https://gourepressure.com/collections/rosin-bags rosin bag and placed between the plates, which are then squeezed together with several tons of force. The resinous sap (which contains the active compounds) is separated from the plant and filtered through the rosin bags, leaving most traces of plant material behind. The resulting extract is then pushed out from between the hot plates and collected onto parchment paper. It's worth noting that raw flower may also be pressed without a filter bag, particularly in home-based operations. A rosin press does not require solvents to complete the cannabinoid and terpene separation. The resulting extract is known as rosin. Like traditional extracts (wax, shatter, etc.), rosin is a highly concentrated form of cannabis, with THC levels that can easily rise above about 60% and even above about 80%. Depending on the temperature and pressure used, rosin can take on a viscous, waxy, or glass-like consistency, minus the solvents.

Water extraction techniques include, but are not limited to, ice water extraction and solventless water extraction. Ice water extraction involves ice, water, and fermentation and utilizes ice water/baths to extract and produce a cannabinoid and/or terpene distillate. Ice water extraction is the process of removing cannabinoid laden trichomes from plant material by washing the material in cold water. Ice water extraction applies the theory that cannabinoids are denser than water. Once plants are harvested the trim harvested therefrom after the flowers are trimmed is immediately frozen to preserve the resin and keep the leaf from drying out. If the leaf dries during the washing process it is more likely to break apart and add contaminant to the hash, which would have to be cleaned out later. The frozen material is then washed. The plant material is added to ice cold water and then agitated causing the dense resin glands to separate from the leaf material and slowly drop to the bottom of the container. The resulting cannabinoid laden water solution may then be filtered through a series of various size bags. Ice water extraction is a solvent less or non-volatile solvent form of extraction, which makes the resin brittle so it can be easily separated. This process is extremely clean and creates a pure, clean product, high in cannabinoids with no chemical residue. The resulting wash is then filtered (e.g., with a mesh screen) leaving the final product in the filter media, which is then dried and ready to use.

The process of synthesizing cannabinoids and adding terpenes, can include, but is not limited to, cannabinoid synthesis using (−)-verbenol, p-Mentha-2,8-dien-1-ol for THC isomers, p-Menth-2-ene-1,8-diol for 6-hydroxy-CBD and $\Delta^9$-THC, syntheses using (+)-trans-2- and (+)-trans-3-carene epoxides, cis-chrysanthenol in the synthesis of (−)-trans-$\Delta^9$-THC, (+)-apoverbenone for the preparation of oxidized $\Delta^{8,9}$-THC, CBD synthesis using (R)-2,9-dibromocamphor, Carveol for the synthesis of hexahydrocannabinols, α-iodocyclohexenones, concentrated approaches, pericyclic reactions, the Ireland-Claisen rearrangement, the molybdenum-catalyzed allylic alkylation reaction, the $S_N2$ arylation of α-iodocyclohexanone and/or NHC-catalysed (4+2) annulation reaction for the enantioselective synthesis of β-lactones. Once a cannabinoid has been synthesized, terpenes (e.g., in solution) can be combined with the synthesized cannabinoid to create a unique profile.

Cannabinoid distillation techniques include, but are not limited to, the short-path method, wiped film distillation, or combinations thereof. The short-path technique begins with a crude oil that is heated until it vaporizes where it enters a fractional tube and then a condensing tube before entering another flask. The material is separated into "heads," "tails" and "main." The "main" is a much higher concentrate of the desired cannabinoid and the "heads" and "tails" are all those other materials that have now been boiled off. The short-path method uses small batches and experienced operators to ensure that the temperatures are kept at a desired level. This makes the short-path method ideal for smaller operations.

The wiped-film technique boils off unwanted solvent or terpenes where the crude oil is "wiped" along the outside of a heated cylinder. All of the product is heated evenly so that undesirable components boil off at a similar rate. The vapors are then condensed back to a liquid and collected. This process can be repeated to ensure a high-quality product.

The technique of drying plant material can be by air drying or hanging. The hang drying technique involves hanging the cannabis plant upside down from an elevated rack within an enclosed area. Hang-drying exposes the cannabis plant to the open air. The temperature and airflow of the are regularly monitored and controlled. The plants are often hung in a dark and dry area. The plant flowers should be adequately spaced to enable the airflow to carry away moisture particles effectively without attracting mold.

Air drying involves the use of a drying rack. Instead of hanging, the flowers are trimmed from the plant and distributed on an open drawer of a rack having numerous stacked drawers. As with the hanging technique, the racks are positioned within an enclosed area where temperature and air flow are monitored and controlled. After seven days of drying, the cannabis plant is checked to determine whether the branch snaps when it is twisted. If the snapping sound is crispy and sharp, the plant material has been dried properly.

The technique of cannabis decarboxylation involves heating cannabis and hemp to activate the cannabinoids within its buds, trim, leaves, or kief Decarboxylating methods target cannabinoid acids, also known as inactive cannabinoids, found in the plant's trichomes. When cannabis matter undergoes the heating process, the cannabinoid acids' molecular structure changes. When decarboxylated, the acids lose one carboxyl group (—COOH) as carbon dioxide while retaining one hydrogen atom. The carboxyl group lost includes one carbon atom and two oxygen atoms ($CO_2$). When this carboxyl group is removed, the molecular mass of THCA, for example, decreases by about 12 percent turning into the active THC compound. When activated, cannabinoids interact more efficiently with the endocannabinoid system (ECS).

The technique of alcohol extraction is typically performed with either ethanol or isopropyl alcohol. The alcohol extraction technique involves soaking the plant matter in alcohol to dilute the trichomes in the solvent, i.e., in the alcohol. Once dissolved, the plant matter is removed, the solution is filtered, and the alcohol is purged. Isopropyl alcohol or ethanol are the most common alcohols used in alcohol extraction.

In some embodiments, the cannabis plant material can be extracted (or infused) into an oil. Suitable oils include, but are not limited to, coconut oil, olive oil, shea butter, avocado oil, other essential oils, and/or combinations thereof. In one embodiment, an oil extraction method included decarboxylating the cannabis, melting the oil (if in solid form), combining the oil with the decarboxylated cannabis, simmering the cannabis-and-oil mixture for about 1 hour to about 24 hours, about 3 hours to about 6 hours, or any individual value or sub-range within this range, and straining the infused oil in a mesh or strainer, and optionally allowing the infused oil to resolidify.

Suitable methods for growing a cannabis plant according to embodiments herein include planting the cannabis plant. The method further includes growing the cannabis plant for about 14 weeks to about 16 weeks. Finally, the cannabis plant can be harvested and processes according to embodiments herein to extract the cannabinoids and terpenes from the plant.

Further disclosed herein are methods of preparing a composition according to embodiments herein. The methods can include extracting a cannabis component from a cannabis plant using one or more methods as described above.

Further described herein are methods of preparing a dosage form. The methods can include combining one or more component according to embodiments herein with one or more excipients as described herein. The combination or resulting composition as described herein can be processed to form the dosage form. For example, the method can include forming granulating on one or more components, alone or in combination, and forming a matrix of the one or more components. The matrix may then be contained in a tablet, a hard-shell capsule, a soft-shell capsule, a caplet, a sublingual a tablet, a sublingual film, a buccal tablet, a buccal film, a food product, a gummy, a matrix, particles, extrudates, granules, multi-layer tablets, multi-compartment capsules, or combinations thereof. The method can include formulating the composition and/or components for at least one of oral administration, parenteral administration, inhalation, rectal administration, intravaginal administration, sublingual administration, intramuscular injection, transdermal administration, nasal administration, buccal administration, insufflation, or spinal anesthesia.

Methods of Use

Pharmaceutical compositions according to embodiments herein, can be employed for treating a variety of disorders. For example, pharmaceutical compositions as described herein can be administered to treat depression, anxiety and/or various neurological disorders such as post-traumatic stress disorder (PTSD) and Alzheimer's Disease (AD). Phytocannabinoid compounds present within compositions, have been investigated as analgesics, antioxidants, bronchodilatories, Alzheimer disease treatments, ulcer treatments, antipruritics, jaundice treatments, anti-anxiety treatments, anticonvulsants, cancer treatments, addiction treatments, anti-inflammatories, antifungals, psoriasis treatments and sedatives.

According to various embodiments, disclose herein are methods of treating anxiety in a subject in need thereof. The methods can include administering to the subject, at least one of: a composition according to embodiments herein, a component according to embodiments herein, and/or a dosage form according to embodiments herein.

Further disclosed herein is a method of treating depression in a subject. The method can include administering to the subject, at least one of a composition according to embodiments herein, a component according to embodiments herein, and/or a dosage form according to embodiments herein.

Further described is a method of stimulating at least one of positivity of thought or mental function in a subject. The method includes administering to the subject, at least one of:

a composition according to embodiments herein, a component according to embodiments herein, and/or a dosage form according to embodiments herein.

In yet further embodiments, disclosed is a method of treating inflammation in a subject. The method can include administering to the subject, at least one of: a composition according to embodiments herein, a component according to embodiments herein, and/or a dosage form according to embodiments herein.

In further embodiments, disclosed is a method of treating a neurological disorder in a subject. The method can include administering to the subject, at least one of: a composition according to embodiments herein, a component according to embodiments herein, and/or a dosage form according to embodiments herein. Suitable neurological disorders include, but are not limited to, post-traumatic stress disorder (PTSD) and Alzheimer's Disease.

Packaging Systems

In yet further embodiments, disclosed herein are packaging systems comprising compositions, components and/or dosage forms according to embodiments herein. The packaging systems can include a storage component (e.g., a container, a bag, a syringe, etc.) in which the composition(s), component(s) and/or dosage form(s) are placed for storage. The storage containers can be configured to seal preventing exposure of the contents to the external atmosphere. In some embodiments, the container includes therein, thereby or thereon an antioxidant and/or a desiccant to prevent degradation of one or more ingredients (e.g., cannabinoid, terpene, excipient, etc.) within the composition(s), component(s) and/or dosage form(s). The antioxidant and/or desiccant can be in a film, canister, satchel or any other suitable form to permit adsorption of oxygen and/or water. Suitable antioxidants include, but are not limited to, omega-3 fatty acid oils, phenolic compounds optionally with bulky alkyl groups (e.g., t-butyl) added to the aromatic ring, butylated hyroxyanisole (BHA), butylated hydroxytoluene (BHT) and combinations thereof. Suitable desiccants include, but are not limited to, silica gel, clay and molecular sieves.

EXAMPLES

Example 1—the UNIQUE FLOWER ORIGINAL HAZE Cannabis Plant

A UNIQUE FLOWER ORIGINAL HAZE cultivar of *Cannabis sativa*, ssp. *sativa* was grown. Samples were collected and analyzed. The chemotype was isolated via artificial selection and perpetuated via asexual propagation. Samples were harvested at floral maturity and dried to less than 15% moisture content. Floral samples were submitted for chemotype analysis with ChemHistory. The UNIQUE FLOWER ORIGINAL HAZE cannabis plant provided a chemotype profile as set forth in Tables 1-3.

TABLE 1

Composition and Properties of The UNIQUE
FLOWER ORIGINAL HAZE Cannabis Plant

| Property | Concentration by weight based on the total weight of sample |
|---|---|
| Total THC | 17.38% |
| Total CBD | 0.1% |
| β-Myrcene | 0.84% |
| Ocimene 2 | 0.51% |

TABLE 1-continued

Composition and Properties of The UNIQUE
FLOWER ORIGINAL HAZE Cannabis Plant

| Property | Concentration by weight based on the total weight of sample |
|---|---|
| B-Caryophyllene | 0.20% |
| α-Pinene | 0.12% |
| α-Humulene | 0.09% |
| Linalool | 0.06% |
| Limonene | 0.04% |
| Aroma | Fresh/sharp vegetable and herbs, pepper, grains of paradise |
| Psychoactive Effects | Euphoric, thought provoking, mind expanding, uplifting |
| Physiological Effects | Calming |
| Pest Resistance | High |
| Disease Resistance | High |
| Resin Production | Extremely high |

TABLE 2

Cannabinoid Content in UNIQUE FLOWER
ORIGINAL HAZE Cannabis Plant

| Analyte | Mass (%) | Mass (mg/g) |
|---|---|---|
| THCa | 17.77 | 177.7 |
| Δ9-THC | 1.79 | 17.9 |
| THCV | <LOQ | <LOQ |
| CBDa | 0.12 | 1.2 |
| CBD | <LOQ | <LOQ |
| CBDV | <LOQ | <LOQ |
| CBN | <LOQ | <LOQ |
| CBGa | 1.20 | 12.0 |
| CBG | 0.06 | 0.6 |
| CBC | 0.08 | 0.8 |
| Total | 21.01 | 210.1 |

TABLE 3

Terpene Content in UNIQUE FLOWER
ORIGINAL HAZE Cannabis Plant

| Analyte | Mass (%) | Mass (mg/g) |
|---|---|---|
| β-Myrcene | 0.84 | 8.4 |
| Ocimene 2 | 0.51 | 5.1 |
| cis-B-Farnesene | 0.26 | 2.6 |
| β-Caryophyllene | 0.20 | 2.0 |
| α-Pinene | 0.12 | 1.2 |
| α-Humulene | 0.09 | 0.9 |
| Linalool | 0.06 | 0.6 |
| trans-Phytol | 0.05 | 0.5 |
| Limonene | 0.04 | 0.4 |
| Terpinolene | 0.03 | 0.3 |
| (—)-β-Pinene | 0.03 | 0.3 |

Example 2 (Prophetic)—Pharmaceutical Dosage Form Containing a Component of a Unique Flower Original Haze Cultivar A flower of a UNIQUE FLOWER ORIGINAL HAZE cultivar is removed from the plant, dried and ground. First, branches are cut and hung to dry. Once the flowers have reached a moisture content of less than 15%, they are cut from branches and stems. Remaining floral matter is then ground. The dried and ground plant material is weighed to provide a therapeutically effective amount of THC and CBD. The weighed portion of the dried plant material is inserted into a rolling paper to form a combustible dosage form.

Example 3 (Prophetic)—Pharmaceutical Dosage Form Containing a Component of a Unique Flower Original Haze Cultivar An extract from a flower of a UNIQUE FLOWER ORIGINAL HAZE cultivar is prepared using a solvent extraction process. The extract is combined with a pharmaceutically acceptable oil to form a mixture and the mixture is contained within a pharmaceutically acceptable capsule.

Example 4 (Prophetic)—Pharmaceutical Dosage Form

The following dry ingredients were combined in a matrix: about 1 wt % to about 60 wt % tetrahydrocannabinol (THC); about 0.001 wt % to about 50 wt % cannabidiol (CBD); about 0.01 wt % to about 25 wt % β-Myrcene; and about 0.01 wt % to about 25 wt % Ocimene 2. The resulting matrix is compressed into a tablet. Another matrix is prepared having a weight ratio of THC to CBD of about 25:1 to about 10,000:1, of THC to β-Myrcene of about 5:1 to about 10,000:1 and THC to Ocimene 2 of about 5:1 to about 1,000:1. Varying amounts of this matrix are compressed into tablets each representing a different dosage.

Example 5 (Prophetic)—Pharmaceutical Dosage Form

Pharmaceutically acceptable delta (Δ)-9 THC, CBD and one or more other cannabinoids and/or terpenes are synthesized in a laboratory. A dry mixture is prepared to contain about 10 wt % to about 60 wt % of synthetic tetrahydrocannabinol (THC); about 0.001 wt % to about 50 wt % of synthetic cannabidiol (CBD); about 0.01 wt % to about 25 wt % β-Myrcene; and about 0.01 wt % to about 25 wt % Ocimene 2. The resulting mixture is encapsulated in a soft shell and/or hard-shell capsule. Another dry mixture is prepared having a weight ratio of THC to CBD of about 25:1 to about 10,000:1, of THC to β-Myrcene of about 5:1 to about 10,000:1 and THC to Ocimene 2 of about 5:1 to about 1,000:1. Various amounts of this mixture are encapsulated in soft shell and/or hard shell capsules each having a different dosage.

Example 6 (Prophetic)—Pharmaceutical Dosage Form

An extract from a flower of a UNIQUE FLOWER ORIGINAL HAZE cultivar is prepared using a solvent extraction process. The extract is combined with a pharmaceutically acceptable excipient (e.g., an oil, solvent, etc.) to form a mixture and the mixture is contained within a pharmaceutically acceptable inhaler.

Example 7 (Prophetic)—Pharmaceutical Dosage Form

An extract of a flower of a UNIQUE FLOWER ORIGINAL HAZE cultivar is prepared using a solventless extraction process. The flower is granulated, dry sifted and shaken along a screen resulting in a granule size of less than about 200 μm, less than about 100 μm, less than about 60 μm, less than about 50 μm, or less than about 25 μm. Heat and pressure are applied to the cannabis flower, kief, trim and/or granulation and trichomes are received in an extract (e.g., in sappy and amber-hued resin). The extract is combined with a pharmaceutically acceptable excipient and contained within a pharmaceutically acceptable dosage form.

Example 7 (Prophetic)—Pharmaceutical Dosage Form

One or more cannabinoids and terpenes are synthesized and/or extracted from a UNIQUE FLOWER ORIGINAL HAZE plant cultivar. The resulting extract is dosed in a suitable dosage amount into a pharmaceutically acceptable lotion for topical administration.

Exemplary Embodiments

Embodiment 1A. A composition, comprising: a cannabis component, comprising: tetrahydrocannabinol (THC); cannabidiol (CBD); and at least one of β-Myrcene or Ocimene 2.

Embodiment 1B. A composition, comprising: a cannabis component, comprising based on the total weight of the composition: about 10 wt % to about 60 wt % tetrahydrocannabinol (THC); about 0.001 wt % to about 50 wt % cannabidiol (CBD); about 0.01 wt % to about 25 wt % (β-Myrcene; and about 0.01 wt % to about 25 wt % Ocimene 2.

Embodiment 1C. A composition, comprising: a cannabis component, comprising based on the total weight of the composition: about 10 wt % to about 25 wt % tetrahydrocannabinol (THC); about 0.001 wt % to about 1.0 wt % cannabidiol (CBD); about 0.01 wt % to about 5 wt % β-Myrcene; and about 0.01 wt % to about 5 wt % Ocimene 2.

Embodiment 2. The composition of Embodiment 1A, 1B or 1C (collectively referred to as "Embodiment 1"), wherein the THC comprises $\Delta^9$-tetrahydrocannabinol ($\Delta^9$-THC).

Embodiment 3. The composition of Embodiment 1 or 2, comprising at least about 1 mg/g β-Myrcene, at least about 2 mg/g β-Myrcene, at least about 3 mg/g β-Myrcene, at least about 4 mg/g β-Myrcene, at least about 5 mg/g β-Myrcene or at least about 8 mg/g β-Myrcene.

Embodiment 4. The composition of any preceding Embodiment, comprising at least about 1 mg/g to about 15 mg/g β-Myrcene, about 2 mg/g to about 14 mg/g β-Myrcene, about 5 mg/g to about 10 mg/g β-Myrcene or about 6 mg/g to about 8 mg/g β-Myrcene.

Embodiment 5. The composition of any preceding Embodiment, further comprising at least one of: cis-β-Farnesene, 3-Caryophyllene, α-Pinene, (−)-β-Pinene, Limonene, α-Humulene, Linalool, Limonene, trans-Phytol, Terpinolene, a prodrug thereof, a pharmaceutically acceptable salt thereof and combinations of any two or more thereof.

Embodiment 6. The composition of any preceding Embodiment, further comprising, based on the total weight of the composition, at least one of: about 0.01 wt % to about 1.0 wt % cis-β-Farnesene, about 0.01 wt % to about 1.0 wt % β-Caryophyllene, about 0.005 wt % to about 0.5 wt % α-Pinene, about 0.001 wt % to about 0.1 wt % α-Humulene, about 0.001 wt % to about 0.1 wt % Linalool, about 0.001 wt % to about 0.1 wt % Limonene, about 0.01 wt % to about 1.0 wt % trans- Phytol, about 0.01 wt % to about 1.0 wt % Terpinolene, or about 0.01 wt % to about 1.0 wt % (–)-(3-Pinene.

Embodiment 7. The composition of any preceding Embodiment, further comprising at least one cannabinoid (other than THC or CBD).

Embodiment 8. The composition of any preceding Embodiment, further comprising at least one cannabinoid (other than THC or CBD) in an amount of greater than 0 wt % to about 30 wt %, about 0.05 wt % to about 25 wt %, about 0.1 wt % to about 20 wt %, or about 1.0 wt % to about 18 wt % based on the total weight of the composition.

Embodiment 9. The composition of any preceding Embodiment, further comprising at least one of Tetrahydrocannabinolic acid (THCa), $\Delta^9$-tetrahydrocannabinol ($\Delta^9$-THC), $\Delta^9$-Tetrahydrocannabivarin (THCV), Cannabidiolic acid (CBDa), Cannabidiol (CBD), Cannabidivarin (CBDV), Cannabinol (CBN), Cannabigerolic Acid (CBGa), Cannabigerol (CBG), Cannabichromene (CBC), a prodrug thereof, a pharmaceutically acceptable salt thereof or combinations thereof.

Embodiment 10. The composition of any preceding Embodiment, further comprising, based on the total weight of the composition, at least one of: about 5 wt % to about 30 wt %, about 10 wt % to about 25 wt % or about 15 wt % to about 20 wt % Tetrahydrocannabinolic acid (THCa), about 0.1 wt % to about 10 wt %, about 0.5 wt % to about 5 wt % or about 1 wt % to about 2 wt % $\Delta^9$-tetrahydrocannabinol ($\Delta^9$-THC), about 0 wt % to about 1 wt % (THCV), about 5 wt % to about 30 wt %, about 10 wt % to about 25 wt % or about 15 wt % to about 20 wt % Cannabidiolic acid (CBDa), about 5 wt % to about 30 wt %, about 10 wt % to about 25 wt % or about 15 wt % to about 20 wt % Cannabidiol (CBD), about 5 wt % to about 30 wt %, about 10 wt % to about 25 wt % or about 15 wt % to about 20 wt % Cannabidivarin (CBDV), about 5 wt % to about 30 wt %, about 10 wt % to about 25 wt % or about 15 wt % to about 20 wt % Cannabinol (CBN), about 5 wt % to about 30 wt %, about 10 wt % to about 25 wt % or about 15 wt % to about 20 wt % Cannabigerolic Acid (CBGa), about 5 wt % to about 30 wt %, about 10 wt % to about 25 wt % or about 15 wt % to about 20 wt % Cannabigerol (CBG), about 5 wt % to about 30 wt %, about 10 wt % to about 25 wt % or about 15 wt % to about 20 wt % Cannabichromene (CBC), or a prodrug of any of the foregoing, a pharmaceutically acceptable salt of any of the foregoing or combinations of combinations of the foregoing.

Embodiment 11. The composition of any preceding Embodiment, comprising a UNIQUE FLOWER ORIGINAL HAZE cultivar of *Cannabis sativa*, ssp. *sativa*.

Embodiment 12. The composition of any preceding Embodiment, wherein the cannabis component comprises dried cannabis plant material, a cannabis plant extract, a synthetic cannabis component or combinations thereof.

Embodiment 13. The composition of any preceding Embodiment, wherein the composition is a cream, lotion, dentifrice, gum, food product, supplement, alcohol, smoking device, inhalation device, adult use product or extractant.

Embodiment 14A. A cannabis component, comprising, based on the total weight of the cannabis component:

tetrahydrocannabinol (THC); cannabidiol (CBD); and at least one of (β-Myrcene or Ocimene 2.

Embodiment 14B. A cannabis component, comprising, based on the total weight of the cannabis component: about 10 wt % to about 60 wt % tetrahydrocannabinol (THC); about 0.001 wt % to about 50 wt % cannabidiol (CBD); about 0.01 wt % to about 25 wt % β-Myrcene; and about 0.01 wt % to about 25 wt % Ocimene 2.

Embodiment 14C. A cannabis component, comprising, based on the total weight of the cannabis component: about 10 wt % to about 25 wt % tetrahydrocannabinol (THC); about 0.001 wt % to about 1.0 wt % cannabidiol (CBD); about 0.01 wt % to about 5 wt % β-Myrcene; and about 0.01 wt % to about 5 wt % Ocimene 2.

Embodiment 15. The cannabis component of Embodiment 14A, 14B or 14C (collectively referred to as "Embodiment 14"), wherein the THC comprises $\Delta^9$-tetrahydrocannabinol ($\Delta^9$-THC).

Embodiment 16. The cannabis component of Embodiment 14 or 15, comprising at least about 2 mg/g β-Myrcene, at least about 3 mg/g β-Myrcene, at least about 4 mg/g β-Myrcene, at least about 5 mg/g β-Myrcene or at least about 8 mg/g β-Myrcene.

Embodiment 17. The cannabis component of any one of Embodiments 14 to 16, comprising at least about 1 mg/g to about 15 mg/g β-Myrcene, about 2 mg/g to about 14 mg/g β-Myrcene, about 5 mg/g to about 10 mg/g β-Myrcene or about 6 mg/g to about 8 mg/g β-Myrcene.

Embodiment 18. The cannabis component of any one of Embodiments 14 to 17, further comprising at least one of: cis-β-Farnesene, β-Caryophyllene, α-Pinene, (–)-β-Pinene, Limonene, α-Humulene, Linalool, Limonene, trans-Phytol, Terpinolene, a prodrug thereof, a pharmaceutically acceptable salt thereof and combinations of any two or more thereof.

Embodiment 19. The cannabis component of any one of Embodiments 14 to 18, comprising at least one of: about 0.01 wt % to about 1.0 wt % cis-β-Farnesene, about 0.01 wt % to about 1.0 wt % β-Caryophyllene, about 0.005 wt % to about 0.5 wt % α-Pinene, about 0.001 wt % to about 0.1 wt % α-Humulene, about 0.001 wt % to about 0.1 wt % Linalool, about 0.001 wt % to about 0.1 wt % Limonene, about 0.01 wt % to about 1.0 wt % trans-Phytol, about 0.01 wt % to about 1.0 wt % Terpinolene, or about 0.01 wt % to about 1.0 wt % (–)-β-Pinene based on the total weight of the cannabis component.

Embodiment 20. The cannabis component of any one of Embodiments 14 to 19, further comprising at least one cannabinoid (other than THC or CBD).

Embodiment 21. The cannabis component of any one of Embodiments 14 to 20, further comprising at least one cannabinoid (other than THC or CBD) in an amount of greater than 0 wt % to about 30 wt %, about 0.05 wt % to about 25 wt %, about 0.1 wt % to about 20 wt %, or about 1.0 wt % to about 18 wt % based on the total weight of the composition or based on the total weight of the cannabis component.

Embodiment 22. The cannabis component of any one of Embodiments 14 to 21, further comprising at least one of Tetrahydrocannabinolic acid (THCa), $\Delta^9$-tetrahydrocannabinol ($\Delta^9$-THC), $\Delta^9$-Tetrahydrocannabivarin (THCV), Cannabidiolic acid (CBDa), Cannabidiol (CBD), Cannabidivarin (CBDV), Cannabinol (CBN), Cannabigerolic Acid (CBGa), Cannabigerol (CBG), Cannabichromene (CBC), a prodrug thereof, a pharmaceutically acceptable salt thereof or combinations thereof.

Embodiment 23. The cannabis component of any one of Embodiments 14 to 22, further comprising at least one of: about 5 wt % to about 30 wt %, about 10 wt % to about 25 wt % or about 15 wt % to about 20 wt % Tetrahydrocannabinolic acid (THCa), about 0.1 wt % to about 10 wt %, about 0.5 wt % to about 5 wt % or about 1 wt % to about 2 wt % $\Delta^9$-tetrahydrocannabinol ($\Delta^9$-THC), about 0 wt % to about 1 wt % (THCV), about 5 wt % to about 30 wt %, about 10 wt % to about 25 wt % or about 15 wt % to about 20 wt % Cannabidiolic acid (CBDa), about 5 wt % to about 30 wt %, about 10 wt % to about 25 wt % or about 15 wt % to about 20 wt % Cannabidiol (CBD), about 5 wt % to about 30 wt %, about 10 wt % to about 25 wt % or about 15 wt % to about 20 wt % Cannabidivarin (CBDV), about 5 wt % to about 30 wt %, about 10 wt % to about 25 wt % or about 15 wt % to about 20 wt % Cannabinol (CBN), about 5 wt % to about 30 wt %, about 10 wt % to about 25 wt % or about 15 wt % to about 20 wt % Cannabigerolic Acid (CBGa), about 5 wt % to about 30 wt %, about 10 wt % to about 25 wt % or about 15 wt % to about 20 wt % Cannabigerol (CBG), about 5 wt % to about 30 wt %, about 10 wt % to about 25 wt % or about 15 wt % to about 20 wt % Cannabichromene (CBC), or a prodrug of any of the foregoing, a pharmaceutically acceptable salt of any of the foregoing or combinations of combinations of the foregoing.

Embodiment 24. The cannabis component of any one of Embodiments 14 to 23, comprising a UNIQUE FLOWER ORIGINAL HAZE cultivar of *Cannabis sativa*, ssp. *sativa*.

Embodiment 25A. A dosage form comprising: a cannabis component, comprising: tetrahydrocannabinol (THC), cannabidiol (CBD), and at least one of β-Myrcene or Ocimene 2; and a pharmaceutically acceptable excipient.

Embodiment 25B. A dosage form comprising: a cannabis component comprising, based on the total weight of the cannabis component, about 10 wt % to about 60 wt % tetrahydrocannabinol (THC); about 0.001 wt % to about 50 wt % cannabidiol (CBD); and at least one of about 0.01 wt % to about 25 wt % β-Myrcene or about 0.01 wt % to about 25 wt % Ocimene 2; and a pharmaceutically acceptable excipient.

Embodiment 25C. A dosage form comprising: a cannabis component, comprising: about 10 wt % to about 25 wt % tetrahydrocannabinol (THC), about 0.001 wt % to about 1.0 wt % cannabidiol (CBD), and at least one of about 0.01 wt % to about 5 wt % β-Myrcene or about 0.01 wt % to about 5 wt % Ocimene 2; and a pharmaceutically acceptable excipient.

Embodiment 26. The dosage form of Embodiment 25A, 25B or 25C (collectively referred to as "Embodiment 25"), wherein the dosage form is a solid oral dosage form.

Embodiment 27. The dosage form of Embodiment 25 or 26, wherein the dosage form is at least one of a tablet, a hard-shell capsule, a soft-shell capsule, a caplet, a sublingual tablet, a sublingual film, a buccal tablet, a buccal film, a gummy, a matrix, particles, a spray, or combinations thereof.

Embodiment 28. The dosage form of any one of Embodiments 25 to 27, wherein the dosage form is formulated for at least one of oral administration, parenteral administration, inhalation, rectal administration, intravaginal administration, sublingual administration, intramuscular injection, transdermal administration, nasal administration, buccal administration, insufflation, or spinal anesthesia.

Embodiment 29. The dosage form of any one of Embodiments 25 to 28, further comprising a pharmaceutically acceptable excipient.

Embodiment 30. The dosage form of Embodiment 29, wherein the pharmaceutically acceptable excipient comprises at least one of a plasticizer, colorant, lubricant, thermal lubricant, antioxidant, buffering agent, disintegrant, granulating agent, binding agent, diluent, glidant, anti-adherent, sweetener, chelating agent, granulating agent, bulking agent, flavorant, surfactant, solubilizer, stabilizer, hydrophilic polymer, hydrophobic polymer, wax, lipophilic material, absorption enhancer, preservative, absorbent, cross-linking agent, bioadhesive polymer, pore former, osmotic agent, polycarboxylic acid or combinations thereof.

Embodiment 31. The dosage form of any one of Embodiments 25 to 30, wherein the cannabis component comprises dried *Cannabis sativa* plant material.

Embodiment 32. The dosage form of any one of Embodiments 25 to 31, wherein the cannabis component comprises a UNIQUE FLOWER ORIGINAL HAZE cultivar of *Cannabis sativa*, ssp. *sativa*.

Embodiment 33. The dosage form of any one of Embodiments 25 to 32, wherein the THC comprises $\Delta^9$-tetrahydrocannabinol ($\Delta^9$-THC).

Embodiment 34. The dosage form of any one of Embodiments 25 to 33, comprising at least about 2 mg/g β-Myrcene, at least about 3 mg/g β-Myrcene, at least about 4 mg/g β-Myrcene, at least about 5 mg/g β-Myrcene or at least about 8 mg/g β-Myrcene.

Embodiment 35. The dosage form of any one of Embodiments 25 to 34, comprising at least about 1 mg/g to about 15 mg/g β-Myrcene, about 2 mg/g to about 14 mg/g β-Myrcene, about 5 mg/g to about 10 mg/g β-Myrcene or about 6 mg/g to about 8 mg/g β-Myrcene.

Embodiment 36. The dosage form of any one of Embodiments 25 to 35, comprising at least one of: about 0.01 wt % to about 1.0 wt % cis-β-Farnesene, about 0.01 wt % to about 1.0 wt % β-Caryophyllene, about 0.005 wt % to about 0.5 wt % α-Pinene, about 0.001 wt % to about 0.1 wt % α-Humulene, about 0.001 wt % to about 0.1 wt % Linalool, about 0.001 wt % to about 0.1 wt % Limonene, about 0.01 wt % to about 1.0 wt % trans-Phytol, about 0.01 wt % to about 1.0 wt % Terpinolene, or about 0.01 wt % to about 1.0 wt % (−)-β-Pinene based on the total weight of the cannabis component.

Embodiment 37. The dosage form of any one of Embodiments 25 to 36, further comprising at least one cannabinoid (other than THC or CBD).

Embodiment 38. The dosage form of any one of Embodiments 25 to 37, further comprising at least one cannabinoid (other than THC or CBD) in an amount of greater than 0 wt % to about 30 wt %, about 0.05 wt % to about 25 wt %, about 0.1 wt % to about 20 wt %, or about 1.0 wt % to about 18 wt % based on the total weight of the composition or based on the total weight of the cannabis component.

Embodiment 39. The dosage form of any one of Embodiments 25 to 38, further comprising at least one of Tetrahydrocannabinolic acid (THCa), $\Delta^9$-tetrahydrocannabinol ($\Delta^9$-THC), $\Delta^9$-Tetrahydrocannabivarin (THCV), Cannabidiolic acid (CBDa), Cannabidiol (CBD), Cannabidivarin (CBDV), Cannabinol (CBN), Cannabigerolic Acid (CBGa), Cannabigerol (CBG), Cannabichromene (CBC), a prodrug thereof, a pharmaceutically acceptable salt thereof or combinations thereof.

Embodiment 40. The dosage form of any one of Embodiments 25 to 39, further comprising at least one of: about 5 wt % to about 30 wt %, about 10 wt % to about 25 wt % or about 15 wt % to about 20 wt % Tetrahydrocannabinolic acid (THCa), about 0.1 wt % to about 10 wt %, about 0.5 wt % to about 5 wt % or about 1 wt % to about 2 wt % $\Delta^9$-tetrahydrocannabinol ($\Delta^9$-THC), about 0 wt % to about 1 wt % (THCV), about 5 wt % to about 30 wt %, about 10 wt % to about 25 wt % or about 15 wt % to about 20 wt % Cannabidiolic acid (CBDa), about 5 wt % to about 30 wt %, about 10 wt % to about 25 wt % or about 15 wt % to about 20 wt % Cannabidiol (CBD), about 5 wt % to about 30 wt %, about 10 wt % to about 25 wt % or about 15 wt % to about 20 wt % Cannabidivarin (CBDV), about 5 wt % to about 30 wt %, about 10 wt % to about 25 wt % or about 15 wt % to about 20 wt % Cannabinol (CBN), about 5 wt % to about 30 wt %, about 10 wt % to about 25 wt % or about 15 wt % to about 20 wt % Cannabigerolic Acid (CBGa), about 5 wt % to about 30 wt %, about 10 wt % to about 25 wt % or about 15 wt % to about 20 wt % Cannabigerol (CBG), about 5 wt % to about 30 wt %, about 10 wt % to about 25 wt % or about 15 wt % to about 20 wt % Cannabichromene (CBC), or a prodrug of any of the foregoing, a pharmaceutically acceptable salt of any of the foregoing or combinations of combinations of the foregoing.

Embodiment 41A. A *Cannabis sativa* plant, comprising: tetrahydrocannabinol (THC); cannabidiol (CBD); and at least one of $\beta$-Myrcene or Ocimene 2.

Embodiment 41B. A *Cannabis sativa* plant, comprising: about 10 wt % to about 60 wt % tetrahydrocannabinol (THC); about 0.001 wt % to about 50 wt % cannabidiol (CBD); about 0.01 wt % to about 25 wt % $\beta$-Myrcene; and about 0.01 wt % to about 25 wt % Ocimene 2.

Embodiment 41C. A *Cannabis sativa* plant, comprising: about 10 wt % to about 25 wt % tetrahydrocannabinol (THC); about 0.001 wt % to about 1.0 wt % cannabidiol (CBD); about 0.01 wt % to about 5 wt % $\beta$-Myrcene; and about 0.01 wt % to about 5 wt % Ocimene 2.

Embodiment 42. The *Cannabis sativa* plant of Embodiment 41A, 41B or 41C (collectively referred to as "Embodiment 41"), wherein the THC comprises $\Delta^9$-tetrahydrocannabinol ($\Delta^9$-THC).

Embodiment 43. The *Cannabis sativa* plant of Embodiment 41 or 42, comprising at least about 2 mg/g $\beta$-Myrcene, at least about 3 mg/g $\beta$-Myrcene, at least about 4 mg/g $\beta$-Myrcene, at least about 5 mg/g $\beta$-Myrcene or at least about 8 mg/g $\beta$-Myrcene.

Embodiment 44. The *Cannabis sativa* plant of any one of Embodiments 41 to 43, comprising at least about 1 mg/g to about 15 mg/g $\beta$-Myrcene, about 2 mg/g to about 14 mg/g $\beta$-Myrcene, about 5 mg/g to about 10 mg/g $\beta$-Myrcene or about 6 mg/g to about 8 mg/g $\beta$-Myrcene.

Embodiment 45. The *Cannabis sativa* plant of any one of Embodiments 41 to 44, wherein the *Cannabis sativa* plant is a cultivar of *Cannabis sativa*, ssp. *sativa*.

Embodiment 46. The *Cannabis sativa* plant of any one of Embodiments 41 to 45, comprising at least one of:

about 0.01 wt % to about 1.0 wt % cis-$\beta$-Farnesene, about 0.01 wt % to about 1.0 wt % $\beta$-Caryophyllene, about 0.005 wt % to about 0.5 wt % $\alpha$-Pinene, about 0.001 wt % to about 0.1 wt % $\alpha$-Humulene, about 0.001 wt % to about 0.1 wt % Linalool, about 0.001 wt % to about 0.1 wt % Limonene, about 0.01 wt % to about 1.0 wt % trans-Phytol, about 0.01 wt % to about 1.0 wt % Terpinolene, or about 0.01 wt % to about 1.0 wt % (−)-$\beta$-Pinene based on the total weight of the cannabis component.

Embodiment 47. The *Cannabis sativa* plant of any one of Embodiments 41 to 46, further comprising at least one cannabinoid.

Embodiment 48. The *Cannabis sativa* plant of any one of Embodiments 41 to 47, further comprising at least one cannabinoid in an amount of greater than 0 wt % to about 30 wt %, about 0.05 wt % to about 25 wt %, about 0.1 wt % to about 20 wt %, or about 1.0 wt % to about 18 wt % based on the total weight of the composition or based on the total weight of the cannabis component.

Embodiment 49. The *Cannabis sativa* plant of any one of Embodiments 41 to 48, further comprising at least one of Tetrahydrocannabinolic acid (THCa), $\Delta^9$-tetrahydrocannabinol ($\Delta^9$-THC), $\Delta^9$-Tetrahydrocannabivarin (THCV), Cannabidiolic acid (CBDa), Cannabidiol (CBD), Cannabidivarin (CBDV), Cannabinol (CBN), Cannabigerolic Acid (CBGa), Cannabigerol (CBG), Cannabichromene (CBC), a prodrug thereof, a pharmaceutically acceptable salt thereof or combinations thereof.

Embodiment 50. The *Cannabis sativa* plant of any one of Embodiments 41 to 49, further comprising at least one of: about 5 wt % to about 30 wt %, about 10 wt % to about 25 wt % or about 15 wt % to about 20 wt % Tetrahydrocannabinolic acid (THCa), about 0.1 wt % to about 10 wt %, about 0.5 wt % to about 5 wt % or about 1 wt % to about 2 wt % $\Delta^9$-tetrahydrocannabinol ($\Delta^9$-THC), about 0 wt % to about 1 wt % (THCV), about 5 wt % to about 30 wt %, about 10 wt % to about 25 wt % or about 15 wt % to about 20 wt % Cannabidiolic acid (CBDa), about 5 wt % to about 30 wt %, about 10 wt % to about 25 wt % or about 15 wt % to about 20 wt % Cannabidiol (CBD), about 5 wt % to about 30 wt %, about 10 wt % to about 25 wt % or about 15 wt % to about 20 wt % Cannabidivarin (CBDV), about 5 wt % to about 30 wt %, about 10 wt % to about 25 wt % or about 15 wt % to about 20 wt % Cannabinol (CBN), about 5 wt % to about 30 wt %, about 10 wt % to about 25 wt % or about 15 wt % to about 20 wt % Cannabigerolic Acid (CBGa), about 5 wt % to about 30 wt %, about 10 wt % to about 25 wt % or about 15 wt % to about 20 wt % Cannabigerol (CBG), about 5 wt % to about 30 wt %, about 10 wt % to about 25 wt % or about 15 wt % to about 20 wt % Cannabichromene (CBC), or a prodrug of any of the foregoing, a pharmaceutically acceptable salt of any of the foregoing or combinations of combinations of the foregoing.

Embodiment 51. The *Cannabis sativa* plant of any one of Embodiments 41 to 50, further comprising a phenotype for a long flowering period.

Embodiment 52. The *Cannabis sativa* plant of any one of Embodiments 41 to 51, further comprising a phenotype for narrow leaves.

Embodiment 53. The *Cannabis sativa* plant of any one of Embodiments 41 to 52, further comprising a phenotype for looser floral formations.

Embodiment 54. The *Cannabis sativa* plant of any one of Embodiments 41 to 53, further comprising a phenotype for a laxly branched growth form.

Embodiment 55. The *Cannabis sativa* plant of any one of Embodiments 41 to 54, further comprising a phenotype of being more resistant to insects as compared to fast-flowering varieties of *Cannabis sativa.*

Embodiment 56. The *Cannabis sativa* plant of any one of Embodiments 41 to 55, further comprising a phenotype of being more resistant to disease as compared to fast-flowering varieties of *Cannabis sativa.*

Embodiment 57. The *Cannabis sativa* plant of any one of Embodiments 41 to 56, further comprising dense glandular trichomes.

Embodiment 58. The *Cannabis sativa* plant of any one of Embodiments 41 to 57, wherein the *Cannabis sativa* plant produces about 10 resin glands/mm$^2$ to about 60 resin glands/mm$^2$.

Embodiment 59. The *Cannabis sativa* plant of any one of Embodiments 41 to 58, further comprising at least one cannabinoid selected from the group consisting of Tetrahydrocannabinolic acid (THCA), $\Delta^9$-tetrahydrocannabinol ($\Delta^9$-THC), A9-Tetrahydrocannabivarin (THCV), Cannabidiolic acid (CBDa), Cannabidiol (CBD), Cannabidivarin (CBDV), Cannabinol (CBN), Cannabigerolic Acid (CBGa), Cannabigerol (CBG), Cannabichromene (CBC), a prodrug thereof, a pharmaceutically acceptable salt thereof or combinations of any two or more thereof.

Embodiment 60A. A method of growing a cannabis plant, wherein the cannabis plant comprises: tetrahydrocannabinol (THC); cannabidiol (CBD); at least one of β-Myrcene or Ocimene 2, the method comprising: planting the cannabis plant; growing the cannabis plant for about 14 weeks to about 16 weeks; and harvesting the cannabis plant.

Embodiment 60B. A method of growing a cannabis plant, wherein the cannabis plant comprises: about 10 wt % to about 60 wt % tetrahydrocannabinol (THC); about 0.001 wt % to about 50 wt % cannabidiol (CBD); about 0.01 wt % to about 25 wt % β-Myrcene; and about 0.01 wt % to about 25 wt % Ocimene 2, the method comprising: planting the cannabis plant; growing the cannabis plant for about 14 weeks to about 16 weeks; and harvesting the cannabis plant.

Embodiment 60C. A method of growing a cannabis plant, wherein the cannabis plant comprises: about 10 wt % to about 25 wt % tetrahydrocannabinol (THC); about 0.001 wt % to about 1.0 wt % cannabidiol (CBD); about 0.01 wt % to about 5 wt % β-Myrcene; and about 0.01 wt % to about 5 wt % Ocimene 2, the method comprising: planting the cannabis plant; growing the cannabis plant for about 14 weeks to about 16 weeks; and harvesting the cannabis plant.

Embodiment 61A. A method of preparing a composition, comprising: extracting a cannabis component from a cannabis plant, wherein the cannabis component comprises, based on the total weight of the composition: tetrahydrocannabinol (THC); cannabidiol (CBD); at least one of (β-Myrcene or Ocimene 2.

Embodiment 61B. A method of preparing a composition, comprising: extracting a cannabis component from a cannabis plant, wherein the cannabis component comprises, based on the total weight of the composition:

about 10 wt % to about 60 wt % tetrahydrocannabinol (THC); about 0.001 wt % to about 50 wt % cannabidiol (CBD); about 0.01 wt % to about 25 wt % β-Myrcene; and about 0.01 wt % to about 25 wt % Ocimene 2.

Embodiment 61C. A method of preparing a composition, comprising: extracting a cannabis component from a cannabis plant, wherein the cannabis component comprises, based on the total weight of the composition: about 10 wt % to about 25 wt % tetrahydrocannabinol (THC); about 0.001 wt % to about 1.0 wt % cannabidiol (CBD); about 0.01 wt % to about 5 wt % β-Myrcene; and about 0.01 wt % to about 5 wt % Ocimene.

Embodiment 62A. A method of preparing a dosage form, comprising: combining a cannabis component with a pharmaceutically acceptable excipient, wherein the cannabis component comprises: tetrahydrocannabinol (THC); cannabidiol (CBD); and at least one of (β-Myrcene or Ocimene 2.

Embodiment 62B. A method of preparing a dosage form, comprising: combining a cannabis component with a pharmaceutically acceptable excipient, wherein the cannabis component comprises: about 10 wt % to about 60 wt % tetrahydrocannabinol (THC); about 0.001 wt % to about 50 wt % cannabidiol (CBD); about 0.01 wt % to about 25 wt % β-Myrcene; and about 0.01 wt % to about 25 wt % Ocimene 2; and a pharmaceutically acceptable excipient.

Embodiment 62C. A method of preparing a dosage form, comprising: combining a cannabis component with an excipient, wherein the cannabis component comprises, based on the total weight of the composition: about 10 wt % to about 25 wt % tetrahydrocannabinol (THC); about 0.001 wt % to about 1.0 wt % cannabidiol (CBD); about 0.01 wt % to about 5 wt % β-Myrcene; and about 0.01 wt % to about 5 wt % Ocimene; and forming the dosage form.

Embodiment 63. A method of treating anxiety in a subject in need thereof, comprising: administering to the subject, at least one of: a composition according to any one of Embodiments 1 to 16, a cannabis component according to any one of Embodiments 17 to 31, or a dosage form according to any one of Embodiments 32 to 51.

Embodiment 64. A method of treating depression in a subject in need thereof, comprising: administering to the subject, at least one of: a composition according to any one of Embodiments 1 to 16, a cannabis component according to any one of Embodiments 17 to 31, or a dosage form according to any one of Embodiments 32 to 51.

Embodiment 65. A method of stimulating at least one of positivity of thought or mental function in a subject, comprising: administering to the subject, at least one of: a composition according to any one of Embodiments 1 to 16, a cannabis component according to any one of Embodiments 17 to 31, or a dosage form according to any one of Embodiments 32 to 51.

Embodiment 66. A method of treating inflammation in a subject, comprising: administering to the subject, at least one of: a composition according to any one of Embodiments 1 to 16, a cannabis component according to any one of Embodiments 17 to 31, or a dosage form according to any one of Embodiments 32 to 51.

Embodiment 67. A method of treating a neurological disorder in a subject, comprising: administering to the subject, at least one of: a composition according to any one of Embodiments 1 to 16, a cannabis component according to any one of Embodiments 17 to 31, or a dosage form according to any one of Embodiments 32 to 51.

Embodiment 68. The method of Embodiment 67, wherein the neurological disorder is selected from the group consisting of: post-traumatic stress disorder (PTSD) and Alzheimer's Disease.

Definitions

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

As used herein, the terms "about" or "approximately" in connection with a measured quantity refers to the normal variations in that measured quantity, as expected by one of ordinary skill in the art in making the measurement and exercising a level of care commensurate with the objective of measurement and the precision of the measuring equipment. In some embodiments, when "about" or "approximately" is used herein, this is intended to mean that the nominal value presented is precise within ±10%, such that "about 10" would include from 9 to 11. "About" or "approximately," when used in conjunction with a measured quantity, is meant to cover slight variations that may exist in the upper and lower limits of the ranges of the measured quantity so as to not exclude embodiments where on average most of the amounts are satisfied, but where statistically amounts may exist outside the range. It is not the intention to exclude embodiments such as these from the present invention.

As used herein, the term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. In certain embodiments, the term "at least about" includes the recited number minus 10% and any quantity that is higher such that "at least about 10" would include 9 and anything greater than 9. This term can also be expressed as "about 10 or more." Similarly, the term "less than about" typically includes the recited number plus 10% and any quantity that is lower such that "less than about 10" would include 11 and anything less than 11. This term can also be expressed as "about 10 or less."

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as")

provided herein, is intended merely to illuminate certain materials and methods and does not pose a limitation on scope. No language in the specification should be construed as indicating any non-claimed element as essential to the practice of the disclosed materials and methods.

The term "and/or" as used in a phrase such as "A and/or B" herein is intended to include both "A and B" and "A or B".

As used herein, the singular forms "a," "an," and "the" include plural references unless the context clearly indicates otherwise. Thus, for example, reference to "a cannabinoid" includes a single cannabinoid as well as to a mixture of two or more cannabinoids; and reference to a "terpene" includes a single terpene as well as a mixture of two or more terpenes, and the like.

As used herein, the terms "comprises," "comprising," "including," "includes," "containing" and "contains" are to be construed as being inclusive and open ended, and not exclusive. Specifically, when used in this specification and the claims, the terms "comprises," "comprising," "including," "includes," "containing" and "contains" and variations thereof mean the specified features, steps or components are encompassed. These terms are not to be interpreted to exclude the presence of other features, steps or components.

As used herein, the term "composition" includes, but is not limited to, pharmaceutical compositions, a combination of ingredients, a combination of one or more active compounds and a combination of one or more active compounds together with one or more excipients.

As used herein, the term "component" includes, but is not limited to, one or more ingredients, alone or in combination, a plant (e.g., cannabis) part, a plant extract, a dry sieve, a plant oil, raw plant oil, decarboxylated plant oil, filtrate plant oil.

As used herein the term "UNIQUE FLOWER ORIGINAL HAZE cultivar" refers to a *Cannabis sativa*, ssp. *sativa* plant having a particular chemotype and phenotype.

The term "chemotype" as used herein refers to a set of morphological and physiological characteristics within a plant that provide a chemically distinct entity of the plant.

The term "phenotype" as used herein refers to a set of morphological and physiological characteristics within a plant that provide observably distinct characteristics (e.g., height, biomass, leaf shape, color, herbicide tolerance, etc.) of a plant.

As used herein, the terms "active agent," "active ingredient" or "pharmaceutically active ingredient" refers to any material that is intended to produce a therapeutic, prophylactic, or other intended effect, whether or not approved by a government agency for that purpose. This term with respect to a specific agent includes the active agent, including all pharmaceutically active salts, solvates and crystalline forms thereof, where the salts, solvates and crystalline forms.

As used herein, the terms "therapeutically effective" and an "effective amount" refer to that amount of an active agent, or the rate at which it is administered, that is needed to produce a desired therapeutic result.

The term "subject" refers to a human or animal, who has demonstrated a clinical manifestation of a disease or condition. The term "subject" may include a person or animal (e.g., a canine) who is a patient being appropriately treated by a medical caregiver for a disease or condition.

The terms "treatment of" and "treating" include the administration of one or more active agents with the intent to lessen the severity of a disease, condition and/or symptom.

The terms "prevention of" and "preventing" include the avoidance of the onset of a disease or condition by an administration of the active agent.

The term "disease" may be used in a general sense when referring to one or more conditions affecting a physical system (e.g., cardiovascular disease) or a part of the body (e.g., diseases of the foot). The term also may be used in specific senses—for example, a writer might refer in general terms to neurologic disease or in specific terms to Alzheimer's disease. The term "disease" also can be used when referring to a condition that possesses specific characteristics, for example, a condition of the body or a body part that impairs normal functioning and is typically manifested by distinguishing signs and symptoms. "Disease" may be a pathophysiological response to external or internal factors.

The term "condition" as used herein refers to an abnormal state of health that interferes with normal activities or feelings of wellbeing. For example, chronic fatigue syndrome is a neurological condition, diagnosed from a collection of symptoms in addition to the primary symptom of post-exertional malaise.

The term "disorder" as used herein may refer to an irregularity, disturbance or interruption of normal body functions. A "disorder" can be a disruption of a disease of the normal or regular functions in the body or a body part. For example, a disorder resulting from cardiovascular disease is an arrhythmia or irregular heartbeat.

The term "syndrome" refers to a collection or set of symptoms and signs that characterize or suggest a particular disease.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular implementations may vary from these exemplary details and still be contemplated to be within the scope of the present disclosure.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

We claim:

1. A dosage form comprising:
a cannabis component, comprising based on the total weight of the cannabis component:
about 10 wt % to about 25 wt % of tetrahydrocannabinol (THC);
about 0.001 wt % to about 1.0 wt % of cannabidiol (CBD); and at least one of about 0.01 wt % to about 5 wt % β-Myrcene or about 0.01 wt % to about 5 wt % of Ocimene 2;
a plasticizer;
a bulking agent;
a diluent; and
a synthetic excipient.

2. The dosage form of claim 1, wherein the dosage form is a solid oral dosage form.

3. The dosage form of claim 1, wherein the dosage form is at least one of a tablet, a hard-shell capsule, a soft-shell capsule, a caplet, a sublingual tablet, a sublingual film, a buccal tablet, a buccal film, a gummy, a matrix, particles, a spray, or combinations thereof.

4. The dosage form of claim 1, wherein the dosage form is formulated for at least one of oral administration, parenteral administration, inhalation, rectal administration, intravaginal administration, sublingual administration, intramuscular injection, transdermal administration, nasal administration, buccal administration, insufflation, or spinal anesthesia.

5. The dosage form of claim 1, wherein the synthetic excipient comprises at least one of a colorant, boric acid, antioxidant, buffering agent, alginates, granulating agent, stearic acid, silicon dioxide, sodium lauryl sulfate, aspartame, chelating agent, granulating agent, flavorant, surfactant, solubilizer, stabilizer, hydrophilic polymer, hydrophobic polymer, castor wax, lipophilic material, absorption enhancer, preservative, absorbent, cross-linking agent, bioadhesive polymer, pore former, osmotic agent, polycarboxylic acid or combinations thereof.

6. The dosage form of claim 1, wherein the THC comprises A9-tetrahydrocannabinol ($\Delta^9$-THC).

7. The dosage form of claim 1, comprising at least about 1 mg/g to about 15 mg/g β-Myrcene, about 2 mg/g to about 14 mg/g β-Myrcene, about 5 mg/g to about 10 mg/g β-Myrcene or about 6 mg/g to about 8 mg/g β-Myrcene.

8. The dosage form of claim 1, wherein the cannabis component further comprises at least one of:
about 0.01 wt % to about 1.0 wt % cis-β-Farnesene,
about 0.01 wt % to about 1.0 wt % β-Caryophyllene,
about 0.005 wt % to about 0.5 wt % α-Pinene,
about 0.001 wt % to about 0.1 wt % α-Humulene,
about 0.001 wt % to about 0.1 wt % Linalool,
about 0.001 wt % to about 0.1 wt % Limonene,
about 0.01 wt % to about 1.0 wt % trans-Phytol,
about 0.01 wt % to about 1.0 wt % Terpinolene, or
about 0.01 wt % to about 1.0 wt % (–)-β-Pinene based on the total weight of the cannabis component.

9. The dosage form of claim 1, wherein the cannabis component further comprises at least one additional cannabinoid in an amount of, based on the total amount of the cannabis component, greater than 0 wt % to about 30 wt % based on the total weight of the composition or based on the total weight of the cannabis component.

10. The dosage form of claim 1, further comprising at least one of Tetrahydrocannabinolic acid (THCa), $\Delta^9$-tetrahydrocannabinol ($\Delta^9$-THC), $\Delta^9$-Tetrahydrocannabivarin (THCV), Cannabidiolic acid (CBDa), Cannabidiol (CBD), Cannabidivarin (CBDV), Cannabinol (CBN), Cannabigerolic Acid (CBGa), Cannabigerol (CBG), Cannabichromene (CBC), a prodrug thereof, a pharmaceutically acceptable salt thereof or combinations thereof.

11. The dosage form of claim 1, wherein the cannabis component further comprises, based on the total weight of the cannabis component, at least one of:
about 5 wt % to about 30 wt % Tetrahydrocannabinolic acid (THCa), about 0.1 wt % to about 10 wt % $\Delta^9$-tetrahydrocannabinol ($\Delta^9$-THC), about 0 wt % to about 1 wt % (THCV), about 5 wt % to about 30 wt % Cannabidiolic acid (CBDa), about 5 wt % to about 30 wt % Cannabidiol (CBD), about 5 wt % to about 30 wt % Cannabidivarin (CBDV), about 5 wt % to about 30 wt % Cannabinol (CBN), about 5 wt % to about 30 wt % Cannabigerolic Acid (CBGa), about 5 wt % to about 30 wt % Cannabigerol (CBG), about 5 wt % to about 30 wt % Cannabichromene (CBC), or a prodrug of any of the foregoing, a pharmaceutically acceptable salt of any of the foregoing or combinations of combinations of the foregoing.

12. A method of treating anxiety in a subject in need thereof, comprising: administering to the subject, a dosage form according to claim 1.

13. A method of treating depression in a subject in need thereof, comprising: administering to the subject, a dosage form according to claim 1.

14. A method of treating inflammation in a subject, comprising: administering to the subject, a dosage form according to claim 1.

15. A method of treating a neurological disorder in a subject, comprising:

administering to the subject, a dosage form according to claim 1, wherein the neurological disorder is selected from the group consisting of post-traumatic stress disorder (PTSD) and Alzheimer's Disease.

16. The dosage form from claim 1, wherein when a combination of solid oral dosage forms is used, that the forms are administered by an aerosol or an inhaler.

17. The dosage form from claim 1, wherein the plasticizer is allyl glycolate, the bulking agent is mannitol, and the diluent is calcium sulfate dihydrate.

\* \* \* \* \*